(12) United States Patent
Huckle et al.

(10) Patent No.: US 8,123,707 B2
(45) Date of Patent: *Feb. 28, 2012

(54) METHOD AND APPARATUS FOR CONNECTIVE TISSUE TREATMENT

(75) Inventors: James William Huckle, North Yorkshire (GB); Andrew Carter, Acton, MA (US); Nicolas J. Cotton, Westboro, MA (US); William R Walsh, Maroubra (AU); Nelson Scarborough, Germantown, TN (US); Roger J. Talish, Maroubra (GB)

(73) Assignee: Exogen, Inc., Piscataway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/818,452

(22) Filed: Jun. 18, 2010

(65) Prior Publication Data

US 2010/0318003 A1    Dec. 16, 2010

Related U.S. Application Data

(63) Continuation of application No. 10/131,784, filed on Apr. 24, 2002, now Pat. No. 7,789,841, which is a continuation-in-part of application No. 10/096,216, filed on Mar. 11, 2002, now abandoned, which is a continuation of application No. 09/436,999, filed on Nov. 9, 1999, now Pat. No. 6,355,006, which is a continuation of application No. PCT/US98/02447, filed on Feb. 6, 1998, said application No. 10/131,784 is a continuation-in-part of application No. 09/568,481, filed on May 9, 2000, now Pat. No. 6,432,070.

(60) Provisional application No. 60/037,367, filed on Feb. 6, 1997, provisional application No. 60/133,442, filed on May 11, 1999.

(51) Int. Cl.
*A61H 1/00* (2006.01)

(52) U.S. Cl. .......................................................... 601/2

(58) Field of Classification Search ....... 601/2; 600/437
See application file for complete search history.

(56) References Cited

U.S. PATENT DOCUMENTS

| 1,063,782 | A | 6/1913 | Dickey |
| 1,604,870 | A | 10/1926 | Asmara |
| 2,914,829 | A | 12/1959 | Willemain |
| 2,920,853 | A | 1/1960 | Bufogle |
| 3,117,571 | A | 1/1964 | Fry et al. |
| 3,134,451 | A | 5/1964 | Hansen |
| 3,193,034 | A | 7/1965 | Hutchinson et al. |

(Continued)

FOREIGN PATENT DOCUMENTS

AU        19950292        2/2000

(Continued)

OTHER PUBLICATIONS

Patent Abstracts vol. 13, n. 541 (E-854), Dec. 5, 1989.

(Continued)

*Primary Examiner* — Jacqueline Cheng
(74) *Attorney, Agent, or Firm* — Fish & Richardson P.C..

(57) ABSTRACT

The invention relates to methods and apparatus for therapeutically treating connective tissue or increasing vascularization in tissue using ultrasound. More particularly, the present invention relates to methods and apparatus which use ultrasound to stimulate growth or healing, or to treating pathologies, of connective tissue, or to increase vascularization in ischaemic or grafted tissue using ultrasound.

7 Claims, 26 Drawing Sheets

U.S. PATENT DOCUMENTS

| | | |
|---|---|---|
| 3,241,375 A | 3/1966 | Canzonen |
| 3,304,036 A | 2/1967 | Davis |
| 3,310,049 A | 3/1967 | Clynes |
| 3,433,663 A | 3/1969 | Underwood |
| 3,499,437 A | 3/1970 | Balamuth |
| 3,521,225 A | 7/1970 | Kursman et al. |
| 3,550,586 A | 12/1970 | Balamuth |
| 3,575,050 A | 4/1971 | Lynnworth |
| 3,594,993 A | 7/1971 | Heyse |
| 3,664,626 A | 5/1972 | Sneller |
| 3,701,352 A | 10/1972 | Bosworth |
| 3,714,619 A | 1/1973 | Morgan et al. |
| 3,729,162 A | 4/1973 | Salvato |
| 3,760,799 A | 9/1973 | Crowson |
| 3,767,195 A | 10/1973 | Dimick |
| 3,828,769 A | 8/1974 | Mettler |
| 3,855,638 A | 12/1974 | Pilliar |
| 3,890,953 A | 6/1975 | Kraus et al. |
| 3,961,380 A | 6/1976 | Garr |
| 3,986,212 A | 10/1976 | Sauer |
| 4,037,592 A | 7/1977 | Kronner |
| 4,105,017 A | 8/1978 | Ryaby et al. |
| 4,108,165 A | 8/1978 | Kopp et al. |
| 4,127,125 A | 11/1978 | Takemoto et al. |
| 4,141,524 A | 2/1979 | Corvese, Jr. |
| 4,164,794 A | 8/1979 | Spector et al. |
| 4,170,045 A | 10/1979 | Estes |
| 4,176,664 A | 12/1979 | Talish |
| 4,195,517 A | 4/1980 | Kalinoski et al. |
| 4,206,516 A | 6/1980 | Pilliar |
| 4,216,766 A | 8/1980 | Duykers et al. |
| 4,227,111 A | 10/1980 | Cross et al. |
| 4,229,992 A | 10/1980 | McKee et al. |
| 4,233,477 A | 11/1980 | Rice et al. |
| 4,266,532 A | 5/1981 | Ryaby et al. |
| 4,266,533 A | 5/1981 | Ryaby et al. |
| 4,269,797 A | 5/1981 | Mikiya et al. |
| 4,291,025 A | 9/1981 | Pellico |
| 4,296,753 A | 10/1981 | Goudin |
| 4,312,536 A | 1/1982 | Lloyd |
| 4,315,503 A | 2/1982 | Ryaby et al. |
| 4,315,514 A | 2/1982 | Drewes et al. |
| 4,347,645 A | 9/1982 | Iseki |
| 4,351,069 A | 9/1982 | Balhntyn et al. |
| 4,355,428 A | 10/1982 | Deloison et al. |
| 4,358,105 A | 11/1982 | Sweeney, Jr. |
| 4,361,154 A | 11/1982 | Pratt, Jr. |
| 4,365,359 A | 12/1982 | Raab |
| 4,383,533 A | 5/1983 | Bhagat et al. |
| 4,407,044 A | 10/1983 | Iseki |
| 4,410,158 A | 10/1983 | Maffei |
| 4,421,119 A | 12/1983 | Pratt, Jr. |
| 4,431,038 A | 2/1984 | Rome |
| 4,440,025 A | 4/1984 | Hayakawa et al. |
| 4,441,486 A | 4/1984 | Pounds |
| 4,446,586 A | 5/1984 | Reed et al. |
| 4,452,326 A | 6/1984 | Hanssen et al. |
| 4,467,659 A | 8/1984 | Baumoel |
| 4,476,874 A | 10/1984 | Taenzer et al. |
| 4,482,942 A | 11/1984 | Blaisdell et al. |
| 4,511,921 A | 4/1985 | Harlan et al. |
| 4,530,360 A | 7/1985 | Duarte |
| 4,536,894 A | 8/1985 | Galante et al. |
| 4,542,539 A | 9/1985 | Rowe, Jr. et al. |
| 4,542,744 A | 9/1985 | Barnes et al. |
| 4,550,714 A | 11/1985 | Talish |
| 4,556,066 A | 12/1985 | Semrow |
| 4,557,148 A | 12/1985 | Akiyama |
| 4,570,487 A | 2/1986 | Gruber |
| 4,570,640 A | 2/1986 | Barsa |
| 4,570,927 A | 2/1986 | Petrofsky et al. |
| 4,573,996 A | 3/1986 | Kwiatek et al. |
| 4,594,662 A | 6/1986 | Devaney |
| 4,603,146 A | 7/1986 | Kligman |
| 4,612,160 A | 9/1986 | Donlevy et al. |
| 4,627,429 A | 12/1986 | Tsuk |
| 4,630,323 A | 12/1986 | Sage et al. |
| 4,644,942 A | 2/1987 | Sump |
| 4,646,725 A | 3/1987 | Moasser |
| 4,657,543 A | 4/1987 | Langer et al. |
| 4,669,483 A | 6/1987 | Hepp et al. |
| 4,677,438 A | 6/1987 | Michiguchi et al. |
| 4,680,967 A | 7/1987 | Rost |
| 4,687,195 A | 8/1987 | Potts |
| 4,689,986 A | 9/1987 | Carson et al. |
| 4,708,127 A | 11/1987 | Abdelghani |
| 4,710,655 A | 12/1987 | Masaki |
| 4,725,272 A | 2/1988 | Gale |
| 4,726,099 A | 2/1988 | Card |
| 4,763,661 A | 8/1988 | Sommer et al. |
| 4,770,184 A | 9/1988 | Greene, Jr. et al. |
| 4,774,959 A | 10/1988 | Palmer et al. |
| RE32,782 E | 11/1988 | Pratt, Jr. |
| 4,782,822 A | 11/1988 | Ricken |
| 4,787,070 A | 11/1988 | Suzuki et al. |
| 4,787,888 A | 11/1988 | Fox |
| 4,792,336 A | 12/1988 | Hlavacek et al. |
| 4,802,477 A | 2/1989 | Gabbay |
| 4,830,015 A | 5/1989 | Okazaki |
| 4,836,316 A | 6/1989 | Carnevale et al. |
| 4,855,911 A | 8/1989 | Lele et al. |
| 4,858,599 A | 8/1989 | Halpern |
| 4,867,169 A | 9/1989 | Machida et al. |
| 4,877,805 A | 10/1989 | Kligman |
| 4,891,849 A | 1/1990 | Robinson |
| 4,905,671 A | 3/1990 | Senge et al. |
| 4,913,157 A | 4/1990 | Pratt, Jr. et al. |
| 4,917,092 A | 4/1990 | Todd et al. |
| 4,917,376 A | 4/1990 | Lo |
| 4,920,966 A | 5/1990 | Hon et al. |
| 4,926,870 A | 5/1990 | Brandenburger |
| 4,928,959 A | 5/1990 | Bassett et al. |
| 4,930,358 A | 6/1990 | Motegi et al. |
| 4,932,951 A | 6/1990 | Liboff et al. |
| 4,933,230 A | 6/1990 | Card et al. |
| 4,936,303 A | 6/1990 | Detwiler et al. |
| 4,941,474 A | 7/1990 | Pratt, Jr. |
| 4,947,853 A | 8/1990 | Hon |
| 4,979,501 A | 12/1990 | Valchanov et al. |
| 4,982,730 A | 1/1991 | Lewis, Jr. |
| 4,984,462 A | 1/1991 | Hass, Jr. et al. |
| 4,986,275 A | 1/1991 | Ishida et al. |
| 4,993,413 A | 2/1991 | McLeod et al. |
| 4,995,883 A | 2/1991 | Demane et al. |
| 5,000,183 A | 3/1991 | Bonnefous |
| 5,000,442 A | 3/1991 | Dalebout et al. |
| 5,003,965 A | 4/1991 | Talish et al. |
| 5,004,476 A | 4/1991 | Cook |
| 5,016,641 A | 5/1991 | Schwartz |
| 5,018,285 A | 5/1991 | Zolman et al. |
| 5,046,484 A | 9/1991 | Bassett et al. |
| 5,054,490 A | 10/1991 | Rossman et al. |
| 5,067,940 A | 11/1991 | Liboff et al. |
| 5,080,672 A | 1/1992 | Bellis |
| 5,088,976 A | 2/1992 | Liboff et al. |
| 5,099,702 A | 3/1992 | French |
| 5,100,373 A | 3/1992 | Liboff et al. |
| 5,103,806 A | 4/1992 | McLeod et al. |
| 5,106,361 A | 4/1992 | Liboff et al. |
| 5,107,853 A | 4/1992 | Plyter |
| 5,108,452 A | 4/1992 | Fallin |
| 5,133,420 A | 7/1992 | Smith |
| 5,134,999 A | 8/1992 | Osipov |
| 5,139,498 A | 8/1992 | Astudillo Ley |
| 5,140,988 A | 8/1992 | Stouffer et al. |
| 5,143,069 A | 9/1992 | Kwon et al. |
| 5,143,073 A | 9/1992 | Dory |
| 5,154,189 A | 10/1992 | Oberlander |
| 5,163,598 A | 11/1992 | Peters et al. |
| 5,172,692 A | 12/1992 | Kulow et al. |
| 5,178,134 A | 1/1993 | Vago |
| 5,181,512 A | 1/1993 | Viebach et al. |
| 5,184,605 A | 2/1993 | Grzeszykowski |
| 5,186,162 A | 2/1993 | Talish et al. |
| 5,191,880 A | 3/1993 | McLeod et al. |
| 5,197,475 A | 3/1993 | Antich et al. |
| 5,201,766 A | 4/1993 | Georgette |

| | | | | | | |
|---|---|---|---|---|---|---|
| 5,209,221 A | 5/1993 | Riedlinger | | 5,626,554 A | 5/1997 | Ryaby et al. |
| 5,211,160 A | 5/1993 | Talish et al. | | 5,626,630 A | 5/1997 | Markowitz et al. |
| 5,230,334 A | 7/1993 | Klopotek | | 5,630,837 A | 5/1997 | Crowley |
| 5,230,345 A | 7/1993 | Curran et al. | | D380,440 S | 7/1997 | Talish et al. |
| 5,230,646 A | 7/1993 | Thorup | | 5,644,093 A | 7/1997 | Wright et al. |
| 5,230,921 A | 7/1993 | Waltonen et al. | | 5,648,941 A | 7/1997 | King |
| 5,235,981 A | 8/1993 | Hascoet et al. | | 5,656,016 A | 8/1997 | Ogden |
| 5,254,123 A | 10/1993 | Bushey | | 5,665,141 A | 9/1997 | Vago |
| 5,259,384 A | 11/1993 | Kaufman et al. | | 5,680,863 A | 10/1997 | Hossack et al. |
| 5,269,306 A | 12/1993 | Warnking et al. | | 5,690,608 A | 11/1997 | Watanabe et al. |
| 5,273,028 A | 12/1993 | McLeod et al. | | 5,691,960 A | 11/1997 | Gentilman et al. |
| 5,280,728 A | 1/1994 | Sato et al. | | 5,699,803 A | 12/1997 | Carodiskey |
| 5,284,143 A | 2/1994 | Rattner | | 5,702,353 A | 12/1997 | Guzzini et al. |
| 5,285,788 A | 2/1994 | Arenson et al. | | 5,702,389 A | 12/1997 | Taylor et al. |
| 5,295,931 A | 3/1994 | Dreibelbis et al. | | 5,706,818 A | 1/1998 | Gondo |
| 5,301,683 A | 4/1994 | Durkan | | 5,708,236 A | 1/1998 | Shaanan et al. |
| 5,307,284 A | 4/1994 | Brunfeldt et al. | | 5,721,400 A | 2/1998 | Haraldsson et al. |
| 5,309,898 A | 5/1994 | Kaufman et al. | | 5,725,482 A | 3/1998 | Bishop |
| 5,310,408 A | 5/1994 | Schryver et al. | | 5,728,095 A | 3/1998 | Taylor et al. |
| 5,314,401 A | 5/1994 | Tepper | | 5,730,705 A | 3/1998 | Talish et al. |
| 5,316,000 A | 5/1994 | Chapelon et al. | | 5,738,625 A | 4/1998 | Gluck |
| 5,318,561 A | 6/1994 | McLeod et al. | | 5,741,317 A | 4/1998 | Ostrow |
| 5,318,779 A | 6/1994 | Hakamatsuka et al. | | 5,743,862 A | 4/1998 | Izumi |
| 5,322,067 A | 6/1994 | Prater et al. | | 5,752,924 A | 5/1998 | Kaufman et al. |
| 5,323,769 A | 6/1994 | Bommannan et al. | | 5,755,746 A | 5/1998 | Lifshey et al. |
| 5,327,890 A | 7/1994 | Matura et al. | | 5,762,616 A | 6/1998 | Talish |
| 5,330,481 A | 7/1994 | Hood et al. | | 5,779,600 A | 7/1998 | Pape |
| 5,330,489 A | 7/1994 | Green et al. | | 5,785,656 A | 7/1998 | Chiabrera et al. |
| 5,334,214 A | 8/1994 | Putnam | | 5,818,149 A | 10/1998 | Safari et al. |
| 5,339,804 A | 8/1994 | Kemp | | 5,829,437 A | 11/1998 | Bridges |
| 5,340,510 A | 8/1994 | Bowen | | 5,843,741 A | 12/1998 | Wong et al. |
| 5,351,389 A | 10/1994 | Erickson et al. | | 5,856,622 A | 1/1999 | Yamamoto et al. |
| 5,363,850 A | 11/1994 | Soni et al. | | 5,868,649 A | 2/1999 | Erickson et al. |
| 5,366,465 A | 11/1994 | Mirza | | 5,871,446 A | 2/1999 | Wilk |
| 5,367,500 A | 11/1994 | Ng | | 5,886,302 A | 3/1999 | Germanton et al. |
| 5,368,044 A | 11/1994 | Cain et al. | | 5,891,143 A | 4/1999 | Taylor et al. |
| 5,376,065 A | 12/1994 | McLeod et al. | | 5,899,425 A | 5/1999 | Corey Jr. et al. |
| 5,380,269 A | 1/1995 | Urso | | 5,904,659 A | 5/1999 | Duarte et al. |
| 5,386,830 A | 2/1995 | Powers et al. | | 5,906,580 A | 5/1999 | Kline-Schoder et al. |
| 5,393,296 A | 2/1995 | Rattner | | 5,954,675 A | 9/1999 | Dellagatta |
| 5,394,877 A | 3/1995 | Orr et al. | | 5,957,814 A | 9/1999 | Eschenbach |
| 5,394,878 A | 3/1995 | Frazin et al. | | 5,962,790 A | 10/1999 | Lynnworth et al. |
| 5,398,290 A | 3/1995 | Brethour | | 5,971,984 A | 10/1999 | Taylor et al. |
| 5,400,795 A | 3/1995 | Murphy et al. | | 5,984,882 A | 11/1999 | Rosenschein et al. |
| 5,405,389 A | 4/1995 | Conta et al. | | 5,997,490 A | 12/1999 | McLeod et al. |
| 5,409,446 A | 4/1995 | Rattner | | 6,019,710 A | 2/2000 | Dalebout et al. |
| RE34,959 E | 5/1995 | Potts | | 6,022,349 A | 2/2000 | McLeod et al. |
| 5,413,550 A | 5/1995 | Castel | | 6,028,066 A | 2/2000 | Unger |
| 5,415,167 A | 5/1995 | Wilk | | 6,030,386 A | 2/2000 | Taylor et al. |
| 5,417,215 A | 5/1995 | Evans et al. | | 6,048,323 A | 4/2000 | Hon |
| 5,424,550 A | 6/1995 | Kawano et al. | | 6,050,943 A | 4/2000 | Slayton et al. |
| 5,425,954 A | 6/1995 | Thompson et al. | | 6,061,597 A | 5/2000 | Rieman et al. |
| 5,431,612 A | 7/1995 | Holden | | 6,065,350 A | 5/2000 | Hill et al. |
| 5,434,827 A | 7/1995 | Bolorforosh | | 6,068,596 A | 5/2000 | Weth et al. |
| 5,441,051 A | 8/1995 | Hileman et al. | | 6,080,088 A | 6/2000 | Petersen et al. |
| 5,441,058 A | 8/1995 | Fareed | | 6,082,181 A | 7/2000 | Greenwood |
| 5,448,994 A | 9/1995 | Iinuma | | 6,086,078 A | 7/2000 | Ferez |
| 5,458,130 A * | 10/1995 | Kaufman et al. ............ 600/449 | | 6,088,613 A | 7/2000 | Unger |
| 5,460,595 A | 10/1995 | Hall et al. | | 6,093,135 A | 7/2000 | Huang |
| 5,466,215 A | 11/1995 | Lair et al. | | 6,105,431 A | 8/2000 | Duffill et al. |
| 5,468,220 A | 11/1995 | Sucher | | 6,113,559 A | 9/2000 | Klopotek et al. |
| 5,476,438 A | 12/1995 | Edrich et al. | | 6,165,144 A | 12/2000 | Talish et al. |
| 5,478,306 A | 12/1995 | Stoner | | 6,179,797 B1 | 1/2001 | Brotz |
| 5,484,388 A | 1/1996 | Bassett et al. | | 6,190,336 B1 | 2/2001 | Duarte et al. |
| 5,492,525 A | 2/1996 | Gibney | | 6,206,843 B1 | 3/2001 | Iger et al. |
| 5,495,846 A | 3/1996 | Uehara et al. | | 6,213,958 B1 | 4/2001 | Winder |
| 5,496,256 A | 3/1996 | Bock et al. | | 6,234,975 B1 | 5/2001 | McLeod et al. |
| 5,501,657 A | 3/1996 | Feero | | 6,234,990 B1 | 5/2001 | Rowe et al. |
| 5,507,800 A | 4/1996 | Strickland | | 6,251,088 B1 | 6/2001 | Kaufman et al. |
| 5,507,830 A | 4/1996 | DeMane et al. | | 6,258,020 B1 | 7/2001 | Lopez |
| 5,509,933 A | 4/1996 | Davidson et al. | | 6,261,221 B1 | 7/2001 | Tepper et al. |
| 5,520,612 A | 5/1996 | Winder et al. | | 6,261,249 B1 | 7/2001 | Talish et al. |
| 5,524,624 A | 6/1996 | Tepper et al. | | 6,264,650 B1 | 7/2001 | Hovda et al. |
| 5,526,815 A | 6/1996 | Granz et al. | | 6,273,864 B1 | 8/2001 | Duarte et al. |
| 5,541,489 A | 7/1996 | Dunstan | | 6,311,402 B1 | 11/2001 | Brandl et al. |
| 5,547,459 A | 8/1996 | Kaufman et al. | | 6,322,527 B1 | 11/2001 | Talish |
| 5,556,372 A | 9/1996 | Talish et al. | | 6,355,006 B1 | 3/2002 | Ryaby et al. |
| 5,578,060 A | 11/1996 | Pohl et al. | | 6,360,027 B1 | 3/2002 | Hossack et al. |
| 5,615,466 A | 4/1997 | Safari et al. | | 6,394,955 B1 | 5/2002 | Perlitz |

| | | | |
|---|---|---|---|
| 6,397,683 | B1 | 6/2002 | Hagenmeyer et al. |
| 6,406,443 | B1 | 6/2002 | Talish |
| 6,436,060 | B1 | 8/2002 | Talish |
| 6,443,898 | B1 | 9/2002 | Unger et al. |
| 6,464,687 | B1 | 10/2002 | Ishikawa et al. |
| 6,503,214 | B1 | 1/2003 | Talish |
| 6,524,261 | B2 | 2/2003 | Talish et al. |
| 6,685,656 | B1 | 2/2004 | Duarte et al. |
| 6,712,805 | B2 | 3/2004 | Weimann |
| 6,733,468 | B2 | 5/2004 | Talish |
| 6,932,308 | B2 | 8/2005 | Talish et al. |
| 6,960,173 | B2 | 11/2005 | Babaev |
| 7,108,663 | B2 | 9/2006 | Talish |
| 7,211,060 | B1 | 5/2007 | Talish |
| 2002/0016557 | A1 | 2/2002 | Duarte |
| 2002/0068871 | A1 | 6/2002 | Mendlein et al. |
| 2002/0103448 | A1 | 8/2002 | Babaev |
| 2002/0115960 | A1 | 8/2002 | Redding, Jr. |
| 2002/0156400 | A1 | 10/2002 | Babaev |
| 2002/0190136 | A1 | 12/2002 | Babaev |
| 2003/0013956 | A1 | 1/2003 | Michaeli |
| 2003/0153848 | A1 | 8/2003 | Talish |
| 2003/0153849 | A1 | 8/2003 | Huckle |
| 2004/0127790 | A1 | 7/2004 | Lang et al. |
| 2005/0096548 | A1 | 5/2005 | Talish |
| 2006/0106424 | A1 | 5/2006 | Bachem |

FOREIGN PATENT DOCUMENTS

| | | |
|---|---|---|
| CA | 1328485 | 4/1994 |
| DE | 3639263 AI | 6/1987 |
| DE | 4111055 AI | 10/1991 |
| DE | 19613425 | 1/1997 |
| DE | 29811185 U1 | 10/1998 |
| EP | 0 181 506 A2 | 5/1986 |
| EP | 0 331 348 | 9/1989 |
| EP | 0 425 765 AI | 5/1991 |
| EP | 0 536 875 A1 | 4/1993 |
| EP | 0 631 772 | 1/1995 |
| EP | 0 679 371 | 11/1995 |
| EP | 0 695 559 | 2/1996 |
| EP | 0 965 839 | 12/1999 |
| GB | 2 156 983 | 10/1985 |
| GB | 2 263 406 | 7/1993 |
| GB | 2 277 448 | 11/1994 |
| GB | 2 303 552 | 2/1997 |
| JP | SHO 62-47359 | 3/1987 |
| JP | HEI 4-82567 | 3/1992 |
| JP | HEI 4-82569 | 3/1992 |
| JP | HEI5-269159 | 10/1993 |
| JP | 2000 167009 | 6/2000 |
| JP | 2000225161 A | 8/2000 |
| JP | 2000300589 A | 10/2000 |
| WO | 85/03449 | 8/1985 |
| WO | 88/00845 | 2/1988 |
| WO | 88/02250 | 4/1988 |
| WO | 90/06720 | 6/1990 |
| WO | 94/13411 | 6/1994 |
| WO | 95/03744 | 2/1995 |
| WO | 95/33416 | 12/1995 |
| WO | 96/25112 | 8/1996 |
| WO | 96/25888 | 8/1996 |
| WO | 97/33649 | 9/1997 |
| WO | 98/10729 | 3/1998 |
| WO | 98/29036 | 7/1998 |
| WO | 98/34578 | 8/1998 |
| WO | 98/47570 | 10/1998 |
| WO | 99/18876 | 4/1999 |
| WO | 99/22652 | 5/1999 |
| WO | 99/48621 | 9/1999 |
| WO | 99/56829 | 11/1999 |
| WO | 99/58080 | 11/1999 |
| WO | 00/03663 | 1/2000 |
| WO | 00/28925 | 5/2000 |
| WO | WO0047142 A1 | 8/2000 |
| WO | 00/67846 | 11/2000 |
| WO | 00/71207 | 11/2000 |
| WO | 00/76406 | 12/2000 |
| WO | 03/090868 | 11/2003 |
| WO | 2005/007057 | 1/2005 |

OTHER PUBLICATIONS

"Development of Flexible Pieoelectric Transducers and Matching Layers for EXOGEN Incorporated," Final Report, Covering Period Apr. 1, 1997 to Feb. 28, 1998, Rutgers University.

"Generation of Electric Potentials by Bone in Response to Mechanical Stress," *Science Magazine*, 137, 1063-1064 (Sep. 28, 2002).

Abstract, (Proceedings of the 11th Int'l. Conference on Medical and Biological Engineering) "Ultrasonic Stimulation of Fracture Healing", 1976.

Abstract, (Proceedings of the III Congress on Biomedical Engineering) "Ultrasonic Action on Callus Formation in Bones", 1975.

Abstract, (Proceedings of the IV Brazilain Congress on Biomedical Engineering) "Ultrasound in the Treatment of Fractures", 1977.

Arai et al., "The Effect of Ultrasound Stimulation on Disuse Osteoporosis", Brags 17, 1993.

ASTM Designation: C1161-90, "Standard Test Method for Flexural Strength of Advanced Ceramics at Ambient Temperature, " pp. 324-330.(Feb. 1991).

ASTM Designation: D790M-93 Metric, "Standard Test Methods for flexural Properties of Unreinforced and Reinforced Plastics and Electrical Insulating Materials [Metric]", pp. 176-184, (Dec. 1993).

Azuma, ., to, M., Harada, Y., Takagi, H., Ohta, T., Jingushi, S., 2001. Low-intensity pulsed ultrasound accelerates rat femoral fracture healing by acting on the various cellular reactions in the fracture callus. J Bone Miner Res 16, 671-680.

Bascom, "Other Continuous Fibers," 11 8/Constitutent Material Form.

Bascom, "Other Discontinuous Forms," 120/Constituent Material Forms.

Berridge, M.J., "Inositol Trisphosphate and Calcium Signaling", *Nature* (1993), 361:315-325.

Blana et al, "High-intensity focused ultrasound for the treatment of localized prostate cancer: 5-year experience" Feb. 2004, pp. 297-300, vol. 63, No. 2, Urology.

Bloch, "Ultrasound as a Tool for Investigating Bone: Fundamental Principles and Perspectives for Use in Osteoporosis," (1993) Expansion Scientifique Francaise, pp. 787-791.

Bouillet et al, "Efficient cloning of cDNAs of retinoic acid-responsive genes in P19 embryonal carcinoma cells and characterization of a novel mouse gene, Stral (mouse LERK-2/Eplg2)." Aug. 1995, pp. 420-433, vol. 170, No. 2, Developmental Biology.

Brochure: "The Science Behind the Technology," distributed by Smith & Nephew for EXOGEN. (no date).

Buckwalter, J.A., Einhom, T.A., Marsh, J.L., 2001. Bone and Joint Healing. In. Bucholz, R.W., Heckman, J.D. (Eds.), Fractures in Adults. Lippincott, Williams & Wilkins, Philadelphia, 254-256.

Caplan, et al., *Clinical Orthopaedics and Related Research*, No. 342:254-269 (1997).

Cass, "Fabrication of Continuous Ceramic Fiber by the Viscous Suspension Spinning Process," Ceramic *Bulletin*, vol. 70, No. 3, pp. 424-429 (1991).

Chariot et al, "Retinoic acid induces three newly cloned HOXA1 transcripts in MCF7 breast cancer cells." Oct. 13, 1995, pp. 713-720, vol. 215, No. 2, Biochemical and Biophysical Research Communications.

Clark et al, "Ultrasonic therapy for psoriasis" 1995, pp. 58-61, vol. 4, No. 1, Journal of the EPan Academy of Dermatology and Venereology, Netherlands.

Clarke, P.R. et al., "Physical and Chemical Aspects of Ultrasonic Disruption of Cells", *JASA* (1969), 47(2): 649-653.

Clough, R. and J. Simmons, "Theory of Acoustic Emission," Metallurgy Division, national Bureau of Standards. (no date).

Cornejo, et al., "Large-Area Flexible-Array Piezoelectric Ceramic/Polymer composite Transducer for Bone Healing Acceleration," presented at ISAFXI, Montreux, Switzerland (1998).

DeLise, A.M., Fischer, L., Tuan, R.S., 2000. Cellular interactions and signaling in cartilage development. Osteoarthritis Cartilage 8, 309-334.

Doan et al, "In vitro effects of therapeutic ultrasound on cell proliferation, protein synthesis, and cytokine production by human fibroblasts, osteoblasts, and monocytes." Apr. 1999, pp. 409-419, vol. 57, No. 4, Journal of Oral and Maxillofacial Surgery: Official Journal of the American Association of Oral and Maxillofacial Surgeons.
Duarte, L.R., "The Stimulation of Bone Growth by Ultrasound", *Arch. Orthop. Trauma Surg* (1983), 101: 153-159.
Dyson, M. "Therapeutic Applications of Ultrasound", *Biological Effects of Ultrasound* (1985), Nyborg, W.L. and Ziskin, M.C., eds; Churchill Livingstone Inc., New York, Chapter 11.
Einhorn, T.A., 1998. The cell and molecular biology of fracture healing. Clin Orthop Relat Res, S7-21.
El-Mowafi, H., Mohsen, M., 2005. The effect of low-intensity pulsed ultrasound on callus maturation in tibial distraction osteogenesis. Int Orthop 29, 121-124.
Final Report "Treatment of Osteochondral Defects in Rabbits with SAFHS—A Mosaicplasty Model"—EX1098-04R, Prepared by Stephen D. Cook, Ph.D. and Laura P. Patron, B.S.E., Department of Orthopaedic Surgery, Tulane University School of Medicine, pp. 1-22 (Aug. 12, 1999).
Fritton, et al., "Whole-Body Vibration in the Skeleton: Development of a Resonance-Based Testing Device," *Annals of Biomedical Engineering*, vol. 25, pp. 831-839 (1997).
Gold, S.M., Wasserman, R., Preliminary results of tibial bone transports with pulsed low intensity ultrasound (Exogen™). J Orthop Trauma, vol. 19, No. 1, Jan. 2005, 1 page.
Goodship, A.E. et al., "The Influence of Induced Micromovement Upon the Healing of Experimental Tibial Fractures", *J. Bone and Joint Surg.* (1985), 67-B(4): 650-655.
Goodship, et al., "Low magnitude high frequency mechanical stimulation of endochondral bone repair" 43nd Annual Meeting Orthopeadic Research Society, vol. 22, Sec. 1, Feb. 9-13, 1997.
Grabec, "Application of correlation techniques for localization of acoustic emission sources," (1978) *Ultrasonics*, pp. 111-115.
Grabec, et al., "Application of an intelligent signal processing system to acoustic emission analysis," (1989) J. Acoustic Society of America, pp. 1226-1235.
Greenbaum, MA., Kanat, 1.0., 1993. Current concepts in bone healing. Review of the literature. J Am Podiatr Med Assoc 83, 123-129.
Grewe, et al., "Acoustic Properties of Particle Polymer Composite for Ultrasonic Transducer Backing Applications," IEEE Transactions on Ultrasonics, Femoelectrics, and Frequency Control, (1990) vol. 37(6):506-514.
Grewe, Martha G., "Acoustic Matching and Backing Layer for Medical Ultrasonic Transducers," A Thesis in Solid State Science, The Pennsylvania State University; (May 1989), The Center for Ceramics Research, Rutgers.
Gurkan, I., Ranganathan, A., Pleshko, N., Yang, X., Horton, W.E.J., Todman, M., Huckle, J., Spencer, R., 2008. Modification of osteoarthritis in the guinea pig with pulsed low-intensity ultrasound treatment. Osteoarthritis and Cartilage (submitted for review), 1-26.
Gururaja, "Piezoelectrics for Medical Ultrasonic Imaging," *Am. Ceram. Soc. Bull.*, vol. 73, No. 5, pp. 50-55 (May 1994).
Gururaja, T., "Piezoelectric Composite Materials for Ultrasonic Transducer Applications," A Thesis in Solid State Science, The Pennsylvania State University, May 1984.
Hall, et al., "The design and evaluation of ultrasonic arrays using 1-3 connectivity composites," *SPIE*, pp. 216-227, vol. 1733 (1992).
Hanagud, et al., "Acoustic Emission and Diagnosis of Osteoporosis," (1974) *Ultrasonic Symposium Proceedings (IEEE)*, pp. 77-81.
Hanagud, et al., "Acoustic Emission in Bone Substance," (1973) *Biomechanics Symposium Proceedings (ASME)*, pp. 79-81.
Hanagud, et al., "Acoustic Emission Techniques in the Development of a Diagnostic Tool for Osteoporosis," (1975) *Ultrasonic Symposium Proceedings (IEEE)*, pp. 41-45.
Hart, J. "The use of ultrasound therapy in wound healing." Jan. 1998, pp. 25-28, vol. 7. No. 1, Journal of Wound Care.
Hilario, Marluce, "Low-Intensity Ultrasound Radiation in the Tissue Repair of Trophic Leg Ulcers," 1983, University of Sao Paulo, Sao Carlos School of Engineering, pp. 1-125 (Thesis).
Heckman, J.D. et al., "Acceleration of Tibial Fracture Healing by Non-Invasive Low-Intensity Pulsed Utrasound", *J. Bone and Joint Surg.* (1994), 76-A(1): 26-34.
Hill, C.R., "Ultrasonic Exposure Thresholds for Changes in Cells and Tissues", JASA (1972), 52(2): 667-672.

Houle et al, "Retinoic acid regulation of Cdxl: an indirect mechanism for retinoids and vertebral specification." Sep. 2000, pp. 6579-6586, vol. 20, No. 17, Molecular and Cellular Biology.
Howkins, S.D., "Diffusion Rates and the Effect of Ultrasound", *Ultrasonics* (1969), 129-130.
J. Kenwright, et al., "Controlled Mechanical Stimulation in the Treatment of Fibial Fractures," Orthopedics, Clinical Orthopedics and Related Research (1989) 241:36-47.
Jankovich, "The Effects of Mechanical Vibration on Bone Development in the Rat," *J. Biomechanics*, 1972, vol. 5, pp. 241-250.
Ko, "Preform Fiber Architecture for Ceramic-Matrix Composites," Ceramic Bulletin, vol. 68, No. 2, pp. 401-414(1989).
Kristiansen, T.K. et al., "Accerlated Healing of Distal Radial Fractures with the Use of Specific, Low-Intensity Ultrasound", J. Bone and Joint Surg. (1997), 79-A(7) 961-973.
Lagneaux et al, "Ultrasonic low-energy treatment: a novel approach to induce apoptosis in human leukemic cells." Nov. 2002, pp. 1293-1301, vol. 30, No. 11, Experimental Hematology.
Li, J.K., et al, "Cytokine release from osteoblasts in response to ultrasound stimulation." Jun. 2003, pp. 2379-2385, vol. 24, No. 13, Biomaterials.
Liu et al, "FGF8 can activate Gbx2 and transform regions of the rostral mouse brain into a hindbrain fate." Nov. 1999, pp. 4827-4838, vol. 126, No. 21, Development (Cambridge, England).
Lord, "Acoustic Emission—An Update," (1981) *Physical Acoustics*, vol. XV, pp. 295-360.
Martel-Pelletier, J., Lajeunesse, D., Reboul, P., Pelletier, J.-P., 2007. The Role of Subchondral Bone in Osteoarthritis. In: Sharma, L., Berenbaum, F. (Eds.), Osteoarthritis—A Companion to Rheumatology. Elsevier, Philadelphia, 15-19.
Matsuda et al, "Neonatal estrogenization leads to increased expression of cellular retinol binding protein 2 in the mouse reproductive tract." Apr. 2004, pp. 131-139, vol. 316, No. 1, Cell and Tissue Research.
Maurice Hilario, "Low-Intensity Ultrasound Radiation in the Tissue Repair of Trophic Leg Ulcers", 1983, University of Sao Paulo, pp. 1-125.
McLeod, et al., "Improved Postural Stability Following Short Term Exposure to Low Level Whole Body Vibration," 44 Annual Meeting, Orthopaedic Research Society, Mar. 16-19, 1998, New Orleans, Louisiana, p. 89-15, 1 page.
Mitragotri, Samir "Healing sound: the use of ultrasound in drug delivery and other therapeutic applications." Mar. 2005, pp. 255-260, vol. 4, No. 3, Nature Reviews. Drug Discovery.
Moran, et al., *The Journal of Bone and Joint Surgery*, 74-8:659-667 (1992).
Newnham, et al., Connectivity and Piezoelectric-Pyroelectric Composites, Med. Res. Bull., vol. 13, pp. 525-536 (1978).
Niemczewski, B., "A Comparison of Ultrasonic Cavitation Intensity in Liquids," *Ultrasonics*, vol. 18, pp. 107-110, 1980.
Orenberg et al, "Response of chronic psoriatic plagues to localized heating induced by ultrasound" Aug. 1980, pp. 893-897, vol. 116, No. 8, Archives of Dermatology.
Pauer, "Flexible Piezoelectric Material," pp. 1-5, (no date).
Pethica, B.A., et al., Abstract, Biological Repair and Growth Society, Jun. 1998.
Phoenix (Business Wire), Jul. 8, 1997 via CompanyLink—OrthoLogic Corp.
Photographs of Exercise Ergometer Developed by Biodex Medical Systems, Shirley, New York (3 pages,2002).
Photographs of Vibrations Platform Built by Julio Tous, Univiersitat Ramon Lllull, Barcelona, Spain (7 pages, 2002).
Pilgrim, et al., "An Extension of the Composite Nomenclature Scheme, " Med. Res. Bull., vol. 22, pp. 677-684 (1987).
Pilla, A.A. et al., "Non-Invasive Low-Intensity Ultrasound Accelerates Bone Repair: Rabbit Fiubla Model and Human Colles' and Tibial Fractures", *Annual Intl. Conference of IEEE-EMBS Proceedings* (1990),12:1573-1574.
Pilla, et al., "Non-Invasive Low-Intensity Pulsed Ultrasound Accelerates Bone Healing in the Rabbit," *Journal of Orthopaedic Trauma*, vol. 4, No. 3, pp. 246-253 (1990).

Pollock, "Acoustic Emission Inspection," (1992) *ASM Handbook Nondestructive Evaluation and Quality Control*, vol. 17, pp. 278-293.

Pounder, N. M., Harrison, A.J., Low intensity pulsed ultrasound for fracture healing: A review of the clinical evidence and the associated biological mechanism of action. Ultrasonics (2008), doi:10.1016/j.ultras2008.02.005.

Powell, et al., "A Performance Appraisal of Flexible Array Structures Using a Facet Ensemble Scattering Technique," 1991 *Ultrasonic Symposium*, pp. 753-766.

Powell, et al., "Flexible Ultrasonic Transducer Arrays for Nondestructive Evaluation Applications—Part I: The Theoretical Modeling Approach, "*IEEE Transactions on Ultrasonics, Ferroelectrics, and Frequency Control*, vol. 43, No. 3, May 1996, pp. 385-392.

Powell, et al., "Flexible Ultrasonic Transducer Arrays for Nondestructive Evaluation Applications—Part II: Performance Assessment of different Array Configurations," *IEEE Transactions on Ultrasonics, Ferroelectrics, and Frequency Control*, vol. 43, No. 3, May 1996, pp. 393-402.

Progress Report—'Treatment of Osteochondral Defects in Rabbits with SAFHS—Part III, EX1097-01 R, 11 pages (Aug. 26, 1997).

Reher et al, "Effect of ultrasound on the production of IL-8, basic FGF and VEGF" Jun. 1999, s. 416-423, vol. 11, No. 6, Cytokine.

Reher et al, "Ultrasound stimulates nitric oxide and prostaglandin E2 production by human osteoblasts." Jul. 2002, pp. 236-241, vol. 31, No. 1, BONE.

"Reflex Sympathetic Dystrophy, Does RSD Exist?" www.arbon.com (Jun. 4, 1997).

"Reflex Sympathetic Dystrophy: The Pain That Doesn't Stop," tcc.cc.nc.us (Jun. 4, 1997).

RSDnet.org "Reflex Sympathetic Dystrophy Frequently Asked Questions," www.rsdnet.org, six pages (Jun. 4, 1997).

RSDnet.org "Reflex Sympathetic Dystrophy," www.rsdnet.org, four pages (Jun. 4, 1997).

Rutten, S., Nolte, P.A., Korstjens, C.M., van Duin, M.A., Klein-Nulend, J., 2008. Low-intensity pulsed ultrasound increases bone volume, osteoid thickness and mineral apposition rate in the area of fracture healing in patients with a delayed union of the osteotomized fibula. Bone, 1-7.

Safari, "Development of piezoelectric composites for transducers," *J. Phys.France*, 4:1129-1149 (1994).

Sakurakichi, K., Tsuchiya, H., Uehara, K., Yamashiro, T., Tomita, K., Azuma, Y., 2004. Effects of timing of low-intensity pulsed ultrasound on distraction osteogenesis. J Orthop Res 22, 395-403.

Sarvazyan, "Some General Problems of Biological Action of Ultrasound," IEEE Transactions on Sonics and Ultrasonics, vol. 30, No. 1, Jan. 1983.

Schortinghuis et al, "Ultrasound stimulation of maxillofacial bone healing." 2003, pp. 63-74, vol. 14, No. 1, Critical Reviews in Oral Biology and Medicine: An Official Publication of the American Association of Oral Biologists.

Selfridge, "Approximate Material Properties in Isotropic Materials," *IEEE Transactions on Sonics and Ultrasonics*, May 9, 1985).

Shimazaki, A., Inui, K., Azuma, Y., Nishimura, N., Yamano, Y., 2000. Low-intensity pulsed ultrasound accelerates bone maturation in distraction osteogenesis in rabbits. J Bone Joint Surg Br 82, 1077-1082.

Simmons and Clough, 'heory of Acoustic Emission, Metallurgy Division, National Bureau of Standards 17, pages. (undated).

Souquet, et al., "Design of Low-Loss Wide-Band Ultrasonic Transducers for Noninvasive Medical Application," *IEEE Transactions on Sonics and Ultrasonics*, pp. 75-81, vol. SU-26, No. 2, Mar. 1979.

Summary Report 'Treatment of Osteochondral Defects in Rabbits with SAFHS—Parts I and II, EX1095-01 R, EX1096-01 R Prepared by Stephen D. Cook, Ph.D. and Samantha L. Salkeld, Department of Orthopaedic Surgery, Tulane University School of Medicine, pp. 1-41 (Jan. 9, 1997).

Tavakoli and Evans , "The Effect of Bone Structure on Ultrasonic Attenuation and Velocity," *Ultrasonics*, vol. 30, No. 6 (1992).

Ter Haar, G., et al., "Basic Physics of Therapeutic Ultrasound", *Physiotherapy* (1987), 73(3): 110-113.

Tiidus, P.M., "Massage and ultrasound as therapeutics modalities in exercise-induced muscle damage.", Jun. 1999, pp. 267-278, vol. 24, No. 3. Canadian Journal of Applied Physiology= Revue Canadienne de Physiologie Appliquee.

Tis, J.E., Meffert, C.R., Inoue, N., McCarthy, E.F., Machen, M.S., McHale, K.A., Chao, E.Y., 2002. The effect of low intensity pulsed ultrasound applied to rabbit tibiae during the consolidation phase of distraction osteogenesis. J Orthop Res 20, 793-800.

Tsumaki, N., Kakiuchi, M., Sasaki, J., Ochi, T., Yoshikawa, H., 2004. Low-intensity pulsed ultrasound accelerates maturation of callus in patients treated with opening-wedge high tibial osteotomy by hemicallotasis. J Bone Joint Surg Am 86-A, 2399-2405.

Uchio Kozue et al, "Cellular retinol-binding protein-1 expression and modulation during in vivo and in vitro myofibroblastic differentiation of rat hepatic stellate cells and portal fibroblasts." May 2002, pp. 619-628, vol. 82, No. 5, Laboratory Investigation; A Journal of Technical Methods and Pathology.

Wallace, A.L.; Draper E.R.C.; Strachan, R.K.; McCarthy, I.D.; Hughes, S.P.F., "The Vascular Response to Fracture Micromovement", *Clinical Orthopaedics and Related Research* (1994), 301: 281-290.

Waller, et al., "Poling of Lead Zirconate Titanate Ceramics and Flexible Piezoelectric Composites by the Corona Discharge Technique," *J. Am. Ceram. Soc.*, 72(2):322-24 (1989).

Walsh, W.R, Stephens, P., Vizesi F. Bruce, Huckle, J., Yu, 2007. Effects of low-intensity pulsed ultrasound on tendon-bone healing in an intra-articular sheep knee model. Arthroscopy 23, 197-204.

Wang, S.J. et al., "Low-Intensity Ultrasound Treatment Increases Strength in a Rat Femoral Fracture Model", J. *Ortho* Research (1994), 12: 40-47.

Warden et al, "Acceleration of fresh fracture repair using the sonic accelerated fracture healing system (SAFHS): a review.", Feb. 2000, pp. 157-163, vol. 66, No. 2, Calcified Tissue International.

Webster, D.F.et al., "The Role of Ultrasound-Induced Cavitation in the 'In Vitro' Stimulation of Collagen Synthesis in Human Fibroblasts", *Ultrasonics* (1980), 33-37.

Winder, Alan, "Acoustic Emission Monitoring for the Detection, Localization and Classification of Metabolic Bone Disease," Acoustic Sciences Associates, Dec. 1995.

Winder, Alan, "Synthetic Structural Imaging and Volume Estimation of Biological Tissue Organs," Acoustic Sciences Associates, Dec. 1995.

Wu and Cubberly, "Measurement of Velocity and Attenuation of Shear Waves in Bovine Compact Bone Using Ultrasonic Spectroscopy," Med. & Biol., vol. 23, No. 1,129-134,1997.

Y. Qin, et al., "Correlation of In Vivo Bone Adaptation and Mechanical Parameters Using Low Magnitude, High Frequency Loading," 411 Annual Meeting Orthopaedic Research Soc., vol. 20—Sec. 1, Feb. 13-16, 1955, 1 page.

Yang, K.H. et al., "Exposure to Low-Intensity Ultrasound Treatment Increases Aggrecan Gene Expression in a Rat Femur Fracture Model", J. Ortho Research (1996), 14:802-809.

International Search Report mailed Oct. 10, 2005 in International Application No. WO/GB2005/002342, 7 pages.

Office Action issued in U.S. Appl. No. 11/220,128 mailed Feb. 12, 2008, 35 pages.

Office Action issued in U.S. Appl. No. 11/220,128 mailed Mar. 31, 2009, 10 pages.

Office Action issued in U.S. Appl. No. 11/220,128 mailed Jul. 20, 2009.

Office Action issued in U.S. Appl. No. 10/131,784 mailed Oct. 20, 2006, 28 pages.

Office Action issued in U.S. Appl. No. 10/131,784 mailed Oct. 22, 2007, 14 pages.

Office Action issued in U.S. Appl. No. 10/131,784 mailed May 12, 2008, 12 pages.

Office Action issued in U.S. Appl. No. 10/131,784 mailed Jan. 22, 2009, 32 pages.

Office Action issued in U.S. Appl. No. 10/131,784 mailed Jul. 31, 2009, 12 pages.

Office Action for corresponding Japanese Application No. 2003-587491, mailed Aug. 19, 2008, 5 pages.

Office Action for corresponding Japanese Application No. 2003-587491, mailed Mar. 17, 2009, 3 pages.
Office Action for corresponding Japanese Application No. 2003-587491, mailed Jul. 21, 2009, 3 pages.
Official Inquiry for corresponding Japanese Application No. 2003-587491, mailed Sep. 7, 2010, 3 pages.
Appeal Decision for corresponding Japanese Application No. 2003-587491, mailed May 10, 2011, 7 pages.
Office Action issued in U.S. Appl. No. 11/220,128 mailed Mar. 11, 2010.
Office Action issued in U.S. Appl. No. 11/220,128 mailed Mar. 2, 2011.
Office Action issued in U.S. Appl. No. 11/220,128 mailed Aug. 5, 2011.
Office Action issued in U.S. Appl. No. 11/570,828 mailed Mar. 30, 2010.
Office Action issued in AU Application No. 2005205820 mailed Oct. 7, 2010, 3 pages.
Office Action issued in AU Application No. 2005205820 mailed Apr. 12, 2010, 3 pages.
Office Action issued in U.S. Appl. No. 11/220,128 mailed Jul. 9, 2010.

* cited by examiner

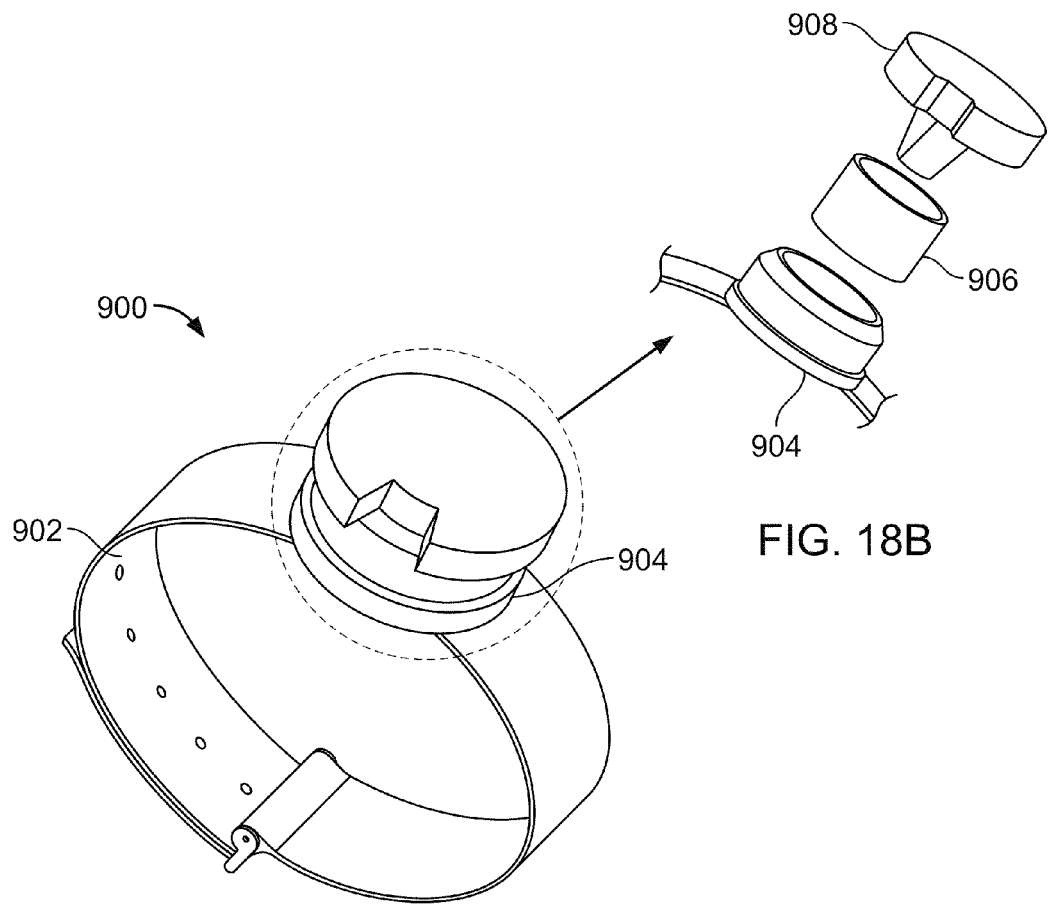
FIG. 18B
FIG. 18A
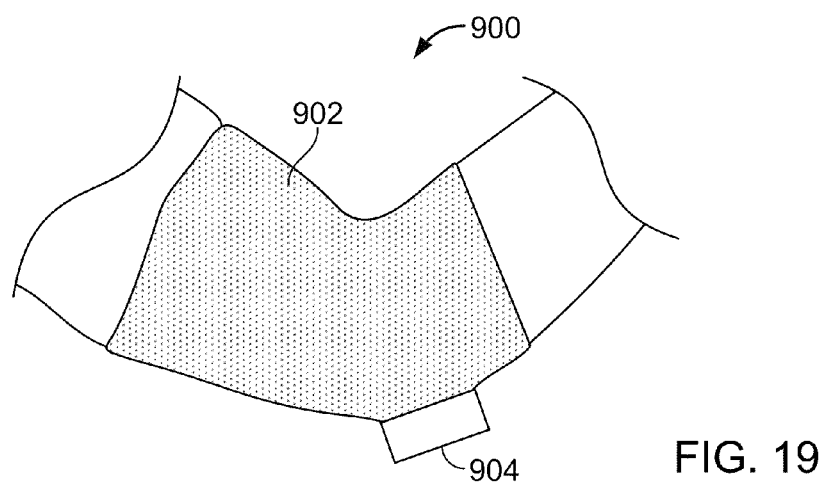
FIG. 19

Medial tibial plateau

Medial tibial plateau

METHOD AND APPARATUS FOR CONNECTIVE TISSUE TREATMENT

CROSS-REFERENCE TO RELATED APPLICATIONS

This application is a continuation application, of and claims priority to, U.S. application Ser. No. 10/131,784, filed Apr. 24, 2002, now pending, which is a continuation of U.S. Ser. No. 10/096,216, filed Mar. 11, 2002, now abandoned, which is a continuation of Ser. No. 09/436,999, filed Nov. 9, 1999, now U.S. Pat. No. 6,355,006, which is a continuation of International Application No. PCT/US98/02447, filed Feb. 6, 1998, which claims priority to U.S. Provisional Application No. 60/037,367 filed on Feb. 6, 1997, and which is a continuation-in-part of U.S. application Ser. No. 09/568,481 filed May 9, 2000, now U.S. Pat. No. 6,432,070, which claims priority to U.S. Provisional Application No. 60/133,442, filed May 11, 1999, the entire contents of each of which are incorporated herein by reference.

BACKGROUND OF THE INVENTION

1. Field of the Invention

The present invention relates to methods and apparatus for therapeutically treating connective tissue and/or increasing vascularization in tissue using ultrasound. More particularly, the present invention relates to methods and apparatus which use ultrasound to stimulate growth or healing, or to treating and/or preventing pathologies of connective tissue, or to increase vascularization in ischaemic or grafted tissue using ultrasound.

2. Description of the Related Art

The use of ultrasound to therapeutically treat and evaluate bone injuries is known. Impinging ultrasonic pulses having appropriate parameters, e.g., frequency, pulse repetition, and amplitude, for suitable periods of time and at a proper external location adjacent to a bone injury has been determined to accelerate the natural healing of, for example, bone breaks and fractures.

U.S. Pat. No. 4,530,360 to Duarte describes a basic non-invasive therapeutic technique and apparatus for applying ultrasonic pulses from an operative surface placed on the skin at a location adjacent to a bone injury. To apply the ultrasound pulses during treatment an operator must manually hold the applicator in place until the treatment is complete.

The Duarte patent as well as U.S. Pat. No. 5,520,612 to Winder et al. describe ranges of RF signal for creating the ultrasound, ultrasound power density levels, ranges of duration for each ultrasonic pulse, and ranges of ultrasonic pulse frequencies.

U.S. Pat. No. 5,003,965 to Talish et al. relates to an ultrasonic body treatment system having a body-applicator unit connected a remote control unit by sheathed fiber optic lines. The signal controlling the duration of ultrasonic pulses and the pulse repetition frequency are generated apart from the body-applicator unit. Talish et al. also describes a mounting fixture for attaching the body-applicator unit to a patient so that the operative surface is adjacent the skin location.

While the systems described in these patents relate to therapeutic methods and apparatus for ultrasonic treatment of hard and soft issue injuries and defects, there is a need for ergonomically configured signal generators and transducers for the treatment of cartilage and/or osteochondral injuries and/or defects and/or for the treatment of cartilage/degenerative joint diseases, such as osteoarthritis (OA). Further, a need exists for an apparatus which optimizes the treatment of cartilage and/or osteochondral injuries and/or defects and/or the treatment of cartilage/degenerative joint diseases, such as osteoarthritis.

A cartilage and/or osteochondral injury and/or defect and/or degenerative joint disease, such as osteoarthritis, typically involves damage to the cartilage which lines articulating bones (articular cartilage), such as the bones of the knee, elbow, shoulder and ankle. Osteochondral injuries can be treated by chondral and/or osteochondral drilling causing blood flow at the site. The aim of chondral drilling is to stimulate cartilage regeneration as part of the healing process. However, the resulting nonhyaline or fibrocartilage produced is biomechanically inferior to articular cartilage, does not have comparable proteoglycan content, and may consist primarily of a thin unorganized layer of collagen. Further, it has been observed that degeneration of the new tissue generally occurs over time, requiring the need for additional reconstructive surgical treatment.

Other methods of treatment include: the transplantation of non-weight bearing cartilage to the injury and/or defect site; inducing a fracture at the injury and/or defect site; placing a carbon fiber matrix to induce cartilage formation; and autologous chondrocyte implantation (ACI). ACI entails removing chondrocytes capable of regenerating hyaline-like cartilage from the body and culturing them for several weeks. During the culture process, the number of cells increases approximately 15 times that of the original tissue sample. The cultured cells are then transplanted through an arthrotomy. A small piece of periosteum, the skin covering a bone, is taken from the patient's tibia. The periosteum is then sutured over the defect to provide a protective cover for the cultured cells. The cultured cells are injected under the periosteum into the defect where they will continue to multiply and produce a durable repair tissue. However, ACI increases the healing time since the chondrocytes need to be cultured before they are transplanted to the patient.

Therefore, there is a further need for a method and apparatus to stimulate cartilage regeneration which produces a repair tissue that is fibrocartilage or hyaline-like, and which is equivalent to articular cartilage in mechanical properties. There is also a need for repair tissue that is generally superior in mechanical properties to that generated using conventional techniques, as described above. Further still, a need also exists for an apparatus which stimulates cartilage regeneration and where the regenerated cartilage does not degenerate over time requiring additional treatment or reconstructive surgery. Further, there is a need for an apparatus which stimulates cartilage regeneration and significantly reduces the healing time.

For treatment of degenerative joint diseases such as osteoarthritis, some combination of symptom-modifying drug, physiotherapy with nonsteroidal antiinflammatories (NSAID's), bracing, weight loss, and/or reduced activity are initially used. However, while these approaches may control symptoms, they do not effectively address the underlying damage to connective tissue, such as cartilage. Moreover, the drugs used may cause severe side effects in some patients, which can result in hospitalization and, in some cases, death. It has been reported that an estimated 20,000 OA patients die each year in the United States from gastrointestinal complications associated with NSAID use. If symptoms remain after these treatments, then more invasive treatment methods are often used, such as injection of viscoelastic materials, arthroscopic surgery, or total joint replacement. There remains a need for additional methods and apparatus that treat and repair connective tissue damage, e.g. damage to cartilage, rather than simply control symptoms of osteoarthritis, and that do not have the side effects and/or tolerance problems associated with current pharmaceutical therapies.

However, injuries and pathologies of cartilage are not the only conditions of connective tissue requiring treatment that involve significant healing time. When ligament and tendons rupture the patients have pain and laxity of the joint or muscle. The current repair options available to the surgeon are to replace or reconstruct the damaged tissue with autograft or allograft tissue, augmentation of the tear surfaces with a device, or by fixation of the tissue with devices such as sutures or anchors, or to simply treat symptoms such as pain and inflammation, without resolving the underlying problem. Because of the risks associated with surgery, treatment options that do not necessarily involve surgery would be desirable. In addition, the repaired tissue is often not as strong as the original undamaged tissue, so that methods to increase repair tissue strength and decrease rehabilitation time would also be desirable. The success of therapies involving replacement or reconstructed tissue is often dependent on the body's ability to vascularize the tissue. Increased vascularization will lead to improved, faster healing, while insufficient vascularization can lead to necrosis of the tissue. Thus, methods for increasing vascularization in surgically repaired tissues would be advantageous.

In addition, in allograft or autograft replacement, the graft dies off and is subsequently repopulated and remodeled by infiltrating cells. This is a lengthy process during which time the graft loses strength and is at risk of rerupture or damage. This leads to lengthy rehabilitation times (e.g., a minimum of 6 months for anterior cruciate ligament (ACL) reconstruction). Inhibiting cell death within the graft via stimulation of blood vessel and tissue in-growth would therefore be desirable. This will lead to a faster and stronger repair and reduced rehabilitation time thus the patients will return to full function faster. The phenomenon of "bone tunnel widening" can often present a problem. Improved integration of bone/tissue/ligament interfaces would help to avoid the "windshield wiper effect" posited as a mechanism for bone tunnel widening.

Surgical methods are also typically required to repair menisci in the knee, for example. Increased vascularization of the avascular "white zone" of the menisci is desirable due to the stimulation in healing that results.

As explained above, the current treatments for many or most of these connective tissue injuries/pathologies are either surgical procedures including repair, reconstruction, augmentation, fixation and tissue resection, or the use of drug therapies that reduce the pain and inflammation. These procedures are usually followed by (or combined with) rehabilitation including physiotherapy which will include a series of stretching exercises with a gradual increase in range of motion and loading on the repair tissue. However, physiotherapy is inconvenient, time consuming and relatively expensive, which can lead to problems with patient compliance. There is thus a need in the art for methods of speeding healing and increasing vascularization that lend themselves to use by the patient at home, and do not require a significant amount of time each day.

It is often desirable to address problems such as laxity of joints by modifying tissues such that the collagenous components of connective tissues (joint capsules, tendons, ligaments) are induced to contract, a procedure often termed capsulorraphy. Applying thermal energy to collagen can cause an alteration of the molecular configuration resulting in shrinkage. This results in a shorter structure and a 'tighter' joint. However, the thermal energy incidentally may also damage the tissue resulting in loss of viability of cells, loss of blood supply and reduced mechanical integrity of the structure. Tissue shrinkage procedures have thus had difficulties resulting from decreased biomechanical integrity and long rehabilitation times due to slow healing. This has resulted in the 'modified' tissue being stretched back out prior to its healing and reestablishment of normal biomechanical strength, resulting in the loss of the benefit of the shrinkage procedure. This damage represents a significant disadvantage and has inhibited the use of capsulorraphy and related tissue shrinkage procedures. Faster post-shrinkage repair of tissue would minimize these difficulties and make the technique more widely applicable.

Tissue engineering involves the growth of cells on a scaffold in vitro (outside the body) to produce a graft for the repair of tissues within the body. One of the shortcomings of this approach is that it is not possible to grow a tissue-engineered material (implant, graft or organ) with a vascular supply in vitro. When the tissue-engineered material is placed into the body and stimulated with ultrasound functional blood vessels are stimulated to grow into the tissue-engineered material from the hosts own blood supply. This is a means of vascularization of this implanted material thus retaining the function and viability of the grafted material. There remains a need for methods and apparatus to achieve this vascularization of tissue engineered material.

SUMMARY OF THE INVENTION

The method and apparatus of the invention resolve many of the difficulties associated with conventional therapies described above. In one embodiment, the invention relates to a method for stimulating growth or healing, or treating pathologies, of connective tissue in mammals in need thereof, by subjecting the affected connective tissue to noninvasive, low intensity ultrasound of a frequency and duration sufficient to stimulate growth, healing, or repair of the connective tissue.

In another embodiment, the invention relates to a method for increasing vascularization in ischaemic or grafted tissue (not limited to connective tissue) in mammals in need thereof, by subjecting the affected tissue to noninvasive, low intensity ultrasound of a frequency and duration sufficient to stimulate an increase in vascularization in the ischaemic or grafted tissue.

In another embodiment, the invention relates to an apparatus for effecting the treatment method described herein. The apparatus includes a placement module adapted to secure one or more transducers thereto in a plurality of configurations. The placement module is then secured to a site near the tissue in need of treatment, for example, at the knee, hip, ankle, shoulder, elbow, or wrist, and the transducers actuated to emit ultrasound sufficient to stimulate healing or repair, or to increase vascularization. Further, the present invention also provides an embodiment having a placement module which contains a locking structure for locking in a particular position the articulating bones of a joint undergoing treatment. This embodiment prevents the patient from moving his limbs, for example, moving the femur with respect to the tibia, during treatment.

In another embodiment, the invention relates to an apparatus for positioning one or more ultrasonic transducers with respect to a joint for delivery of ultrasonic therapy thereto, having a covering member adapted to cover at least a portion of the joint or adjacent body members and be secured thereto in a fixed position, wherein the covering member comprises one more receiving areas adapted to receive and hold one or more ultrasonic transducer assemblies in one or more fixed positions relative to the joint or adjacent body member.

Because of the broad applicability of utility of the invention in promoting healing, the method and apparatus described herein are useful in treating patients with a broad range of problems, such as trauma, tissue insufficiency, pain, post-surgical healing, degenerative conditions such as osteoarthritis, and other problems. Moreover, because the invention is portable, does not require prolonged treatment times, and is designed for ease of use and positioning of the ultrasonic transducers, patients will be more likely to use the technique properly and sufficiently to benefit therefrom.

BRIEF DESCRIPTION OF THE DRAWINGS

Specific embodiments of the invention are descried below with reference to the drawings, which are described as follows:

FIG. 14 shows an embodiment of the placement module of the invention suitable for treating the shoulder area.

FIG. 18A is a schematic view of an embodiment of a placement module according to the invention suitable for application of ultrasound to the wrist or hand area. FIG. 18B is a schematic exploded view of the transducer port or assembly;

FIG. 19 is a schematic view of an embodiment of a placement module according to the invention suitable for application of ultrasound to the elbow area.

DETAILED DESCRIPTION OF SPECIFIC EMBODIMENTS

Figure 1:
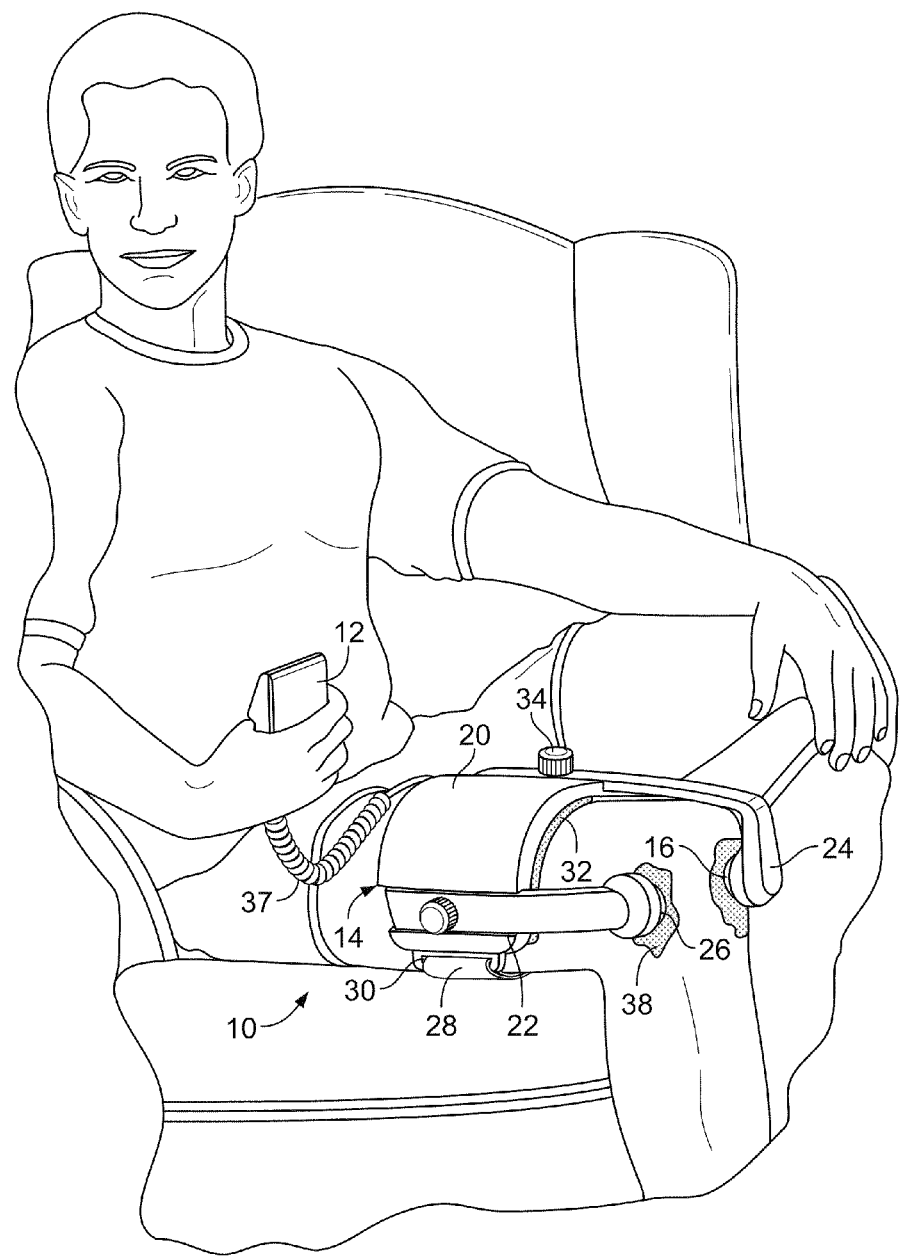
FIG. 1 is a perspective view of a patient wearing one embodiment of a portable ultrasonic treatment apparatus suitable for carrying out the method of the invention having a main operating unit or controller and a placement module.

The ultrasonic treatment apparatus and method of the present invention involves the non-invasive use of low intensity, ultra high-frequency acoustic energy (ultrasound) to treat injuries, defects, or pathologies of connective tissue, or to increase vascularization of ischaemic or grafted tissue. It will be recognized that in treating connective tissue, increased vascularization will likely result and contribute to healing, but that the use of the method and apparatus to increase vascularization is not limited to treatment of connective tissue, but extends to grafted tissues, organs, or engineered tissue that has been produced ex vivo.

As described above, in one embodiment, the invention relates to an apparatus and method for the treatment of injuries and pathologies, and the stimulation of healing, of connective tissues. The method may be used as an adjunct to surgical repair, in order to speed healing, or in some cases can be used alone to heal tissue injuries without surgery (e.g., for degenerative diseases such as osteoarthritis, tendonosis, and tendonitis). The apparatus and method of the invention are particularly suitable for use in treatment of connective tissues associated with joints, such as those in the hand or foot, wrist, ankle (Achilles tendon), knee (e.g., anterior cruciate ligament, posterior cruciate ligament, meniscofemoral ligament, lateral or collateral ligaments, tendon of quadriceps, gracilis tendon, sartorius tendon, seinitendinosis tendon, popliteus tendon, adductor magnus tendon, medial or lateral meniscus), elbow (lateral, collateral, or annular ligaments), hip, shoulder (e.g., supraspinatus tendon/rotator cuff/glenoidal labrum), back and neck.

Nonlimiting examples of conditions or situations in which treatment according to the invention is suitable include degenerative diseases such as osteoarthritis, ligament, tendon, spinal disc and meniscus injuries, ligament and tendon pathologies, surgical repair or modification (including modification procedures such as capsulorraphy (shrinkage), and procedures for shrinkage of the spinal disc (for example the Idet procedure), and for the treatment of ischaemic tissues (such as a myocardially infarcted heart) to increase vascularization by inducing a vascular supply (in-growth of new blood vessels) into these tissues (used herein to refer to tissues that have either a restricted blood flow or a lack of adequate vascular supply). The invention could also be used to increase vascularization in a grafted tissue/organ or into a tissue engineered graft that has been produced ex vivo.

The invention can be used as an adjunct to the surgical repair of ruptured ligament and tendons (for example rotator cuff tendon repair, anterior cruciate ligament, posterior cruciate, lateral collateral ligament, medial collateral, flexor or extensor repairs, Achilles tendon, surgical tendon transfers or tendon weaves).

The invention is suitable for treatment of a number of different tendoniopathies and/or overuse injuries, including without limitation lateral or medial epicondylitis (tennis elbow), carpal tunnel syndrome, plantar fascitis, Achilles tendonitis, and the like, as either an adjunct to surgery, or without surgery.

The invention can also be used to increase the rate, quality and vascularity of connective tissue that is regenerated on, and/or grows into, a scaffold which is implanted into the body to support connective repair/regrowth. The term "scaffold" as used herein means a three dimensional, at least partially porous structure, and having sufficient porosity to allow cell infiltration. The scaffold surface allows cell adhesion and growth such that cell proliferation and extracellular matrix (ECM) generation can occur and tissue can be laid down and remodel.

The scaffolds can be formed from bioresorbable or non-bioresorbable materials. Suitable bioresorbable materials include bioresorbable polymers or copolymers including, for example, polymers and/or copolymers formed from the following monomers or mixtures thereof: hydroxy acids, particularly lactic acid, glycolic acid; caprolactone; hydroxybutyrate; dioxanone; orthoesters; orthocarbonates; and/or aminocarbonates. The bioresorbable materials may also contain natural materials such as collagen, cellulose, fibrin, hyaluronic acid, fibronectin, chitosan or mixtures of two or more of these materials. The bioresorbable materials may also contain devitalised xenograft and/or devitalised allograft material. Bioresorbable ceramics, such mono-, di-, octa-, a-tri-, b-tri and tetra-calcium phosphate, hydroxyapatite, fluoroapatite, calcium sulphate, calcium fluoride, calcium oxide or mixtures of two or more of these materials, may also be used as scaffold material.

Suitable non-bioresorbable materials for use in scaffolds include polyesters, particularly aromatic polyesters, such as polyalkylene terephthalates, like polyethylene terephthalate and polybutylene terephthalates; polyamides; polyalkenes such as polyethylene and polypropylene; poly(vinyl fluoride), polytetrafluoroethylene carbon fibres, silk (natural or synthetic), carbon fibre, glass and mixtures of these materials.

Scaffolds may also be formed from materials that include hydrogels. Examples of suitable hydrogel materials include: poly(oxyethylene)-poly(oxypropylene) block copolymers of to ethylene diamine, polysaccharides, chitosan, poly(vinyl amines), poly(vinyl pyridine), poly(vinyl imidazole), poly-ethylenimine, poly-L-lysine, growth factor binding or cell adhesion molecule binding derivatives, derivatised versions of the above, e.g. polyanions, polycations, peptides, polysaccharides, lipids, nucleic acids or blends, block-copolymers or combinations of the above or copolymers of the corresponding monomers; agarose, methylcellulose, hydroxypropylmethylcellulose, xyloglucan, acetan, carrageenan, xanthan gum/locust bean gum, gelatine, collagen (particularly Type 1), PLURONICS™, POLOXAMERS™, poly (N-isopropylacrylamide) and N-isopropylacrylamide copolymers.

Structurally, the scaffold may be a woven, non-woven (fibrous material), knitted, braided or crocheted material, a foam, a sponge, a dendritic material, or a combination or mixture of two or more of these.

Following surgery, the ultrasound device is applied non-invasively to the outside of the body (e.g., coupled to the skin with coupling media, such as a gel) after surgery in the region of the repaired tissue, and is operated to transmit ultrasound, desirably in the form of pulses, into the tissue in need of treatment, or at the interface with the uninjured tissues. Exposure to the ultrasound stimulates a faster, better quality repair of the tissue. At a bone interface, the ultrasound will also stimulate bone repair and bone in growth into the repair or graft tissue. This gives rise to a faster, stronger repair and improved integration of the interface between, e.g., tendon, ligament and bone.

The method and apparatus of the invention may also be used to non-invasively treat pathologies of connective tissues, such as osteoarthritis, ligament and tendon conditions, without the need for a surgical procedure. Such conditions include, as examples, osteoarthritis, acute tears, chronic overuse injuries, and tendon pathologies including tendonosis and tendonitis. In these cases the device would be applied to the skin in the region of pain above the injured or degenerative tendon or ligament. The ultrasound would then propagate in to the defective tissue and stimulate the tissue to remodel and repair without the requirement for surgery. The treatment thus would improve the in-vivo function of the tissue with respect to mechanical load bearing, and avoid the risks and disadvantages associated with surgery, as described above.

As described above, the method and apparatus of the invention is also particularly suitable for stimulating repair of damaged menisci. This could be done after surgical repair to stimulate the healing process, or as a possible alternative to surgery. Without being bound by any theory, the invention appears to be particularly useful because it stimulates healing of the avascular 'white zone' of the meniscus by stimulating in-growth of blood vessels and their concomitant cell populations, which are capable of healing the damaged tissue. More particularly, the meniscal cartilage is partially vascularized in the external periphery of the tissue and has an avascular inner region. If the vascular region is damaged, it usually heals or can be repaired due to the presence of a blood supply. If the avascular region is damaged, it does not heal and cannot be easily repaired because of the absence of blood supply. As a result, damaged avascular regions often must be resected, which can lead to post meniscectomy arthritis. However, using the method and apparatus of the invention repair of the avascular region becomes possible due to the ability of the invention to stimulate vascularization.

However, the method and apparatus of the invention is not limited to increasing vascularization of damaged menisci, but can also be used to treat general ischaemic tissues which have restricted blood flow and/or a lack of adequate vascular supply. For instance, the method and apparatus of the invention can be used to induce a vascular supply and in growth into a grafted tissue or organ, or into a tissue engineered graft that has been produced ex vivo and lacks a vascular supply. The invention could also be used to treat tissues with a partial vascular supply to stimulate repair of tissues in the avascular region of the tissue.

In addition to surgical and nonsurgical treatment of tissue injuries, defects, or pathologies, the method and apparatus of the invention can also be used as an adjunct to tissue modification treatments, such as capsulorraphy, or shrinkage of the spinal disc and related or similar tissue shrinkage procedures, to significantly increase the success rate and benefit to the patient of undergoing such procedures. As described above, the use of thermal energy to alter the configuration of connective tissue and thereby eliminate joint laxity is associated with problems relating to tissue damage. Loss of cell viability, loss of blood supply, and reduced mechanical integrity can result in loss of many of the benefits associated with the tissue shrinkage procedure.

The method and apparatus of the invention provides a means to address these potentially adverse effects by stimulating revascularization and cell repopulation, resulting in repair and return to normal biomechanical integrity. The invention adds to the ability to shrink the tissue the ability to also rapidly heal it in its shortened configuration, and as a result offers a new treatment option that was previously difficult to achieve. This invention thus makes practical a new treatment method having the significant benefits associated with a reduced surgical procedure, i.e. a less invasive and traumatic procedure, for otherwise difficult to treat cases. The reduction in healing time obtainable with the method and apparatus of the invention means that the chances of the weakened tissue being stretched are reduced. The reduction in rehabilitation time allows the patient to return to normal activities more quickly. The combination of a minimally invasive procedure using radiofrequency tissue shrinkage technology in combination with the method and apparatus of the invention provides a procedure offering dramatically reduced rehabilitation time and an opportunity to treat a broader range of patients and disorders without surgery.

The method and apparatus of the invention can be combined with pharmacological treatment modes, and these combinations also form a part of the invention. For instance, the method of the invention can be used in conjunction with known growth factor therapies, including but not limited to, the Transforming Growth Factor β superfamily, including: TGFβ's, Bone Morphogenetic Proteins (BMP's, e.g. BMP2, BMP4), Cartilage Derived Morphogenic Proteins (CDMP's e.g. CDMP-1, CDMP-2) and Growth Differentiation Factors (e.g. GDF5), angiogenic factors (angiogenin), platelet-derived cell growth factor (PD-ECGF), Platelet Derived Growth Factors (PDGF), Vascular Endothelial Growth Factor (VEGF), the Epidermal Growth Factor family, e.g. EGF, Transforming Growth Factor Alpha (TGFα), Platelet Derived Growth Factors, e.g. PDGF-A, PDGF-B, PDGF-BB, Fibroblast Growth Factors, e.g. BFGF, Hepatocyte Growth Factors (HGF), Insulin-like Growth Factors, e.g. IGF-1, IGF-II, Growth Hormones (GH), Interleukins (e.g. IL-1, IL-11), Connective Tissue Growth Factors (CTGF), Parathyroid Hormone Related Proteins (PTHrp), autologous growth factors (such blood and platelet derived factors), and mixtures of at least two of these materials. In conjunction with growth factor therapies, the method and apparatus of the invention provide a faster, better quality repair. Appropriate dosages of such growth factors are those known in the art for use in therapy without ultrasound treatment.

As described in more detail below, the apparatus of the invention contains one or more ultrasound treatment heads that direct ultrasonic energy to the site of the tissue to be treated through the overlying tissues. Without being bound by any theory, it is believed that the ultrasonic energy provides a mechanical stimulus that induces tissue repair and also stimulates to blood vessel in growth and blood flow to the tissue which aids the healing or repair process. This stimulation appears to be the result of a molecular mechanism related to vascularity through an increase in growth factor and biological molecules known to be vital for angiogenesis, matrix production and cellular proliferation. The pathway may be mediated through signal transduction molecules that regulate cellular function.

The ultrasound is generally a low intensity ultrasound having a frequency ranging between about 1 and about 2 MHz, more particularly about 1.5 MHz. The ultrasound desirably is pulsed, having a pulse width ranging from about 10 to about 2,000 microseconds, more particularly about 200 microseconds, with a repetition frequency ranging from about 0.1 to about 10 KHz, more particularly about 1 KHz.

The ultrasonic energy is emitted by one or more transducers. Multiple transducers are often desirable, in particular for treating some types of ligament injury, and when present can be configured into arrays to properly place them adjacent to areas to be treated. For example ACL surgical repairs can be treated with multiple transducers, each in a separate treatment head. One treatment head is applied to the outside of the knee in the region of the tibial bone tunnel; another treatment head is applied to knee in the region of the mid section of the graft and another treatment head is applied to knee in the region of the femoral bone tunnel. Multiple transducers can also be set to emit energy simultaneously (e.g., in simultaneous pulses) or in a phased fashion, such that they emit pulses sequentially.

One embodiment of the apparatus of the invention includes an ergonomically constructed placement module having a strap or other fastening means for securing it and the attached transducer or treatment head adjacent to the part of a patient's body in need of treatment. At least one ultrasonic transducer assembly is attached or imbedded within the placement module and properly positioned on the various anatomical regions in proximity to the desired treatment site. Different types of ultrasonic transducers and signals can be provided, such as those described and schematically depicted in U.S. Pat. No. 5,520,612 to Winder et al. which is incorporated herein by reference. Particularly, the transducers and arrangements schematically depicted by FIGS. 7-11 of the patent in which at least one transducer is used to provide acoustic energy to the site of the injury. The apparatus may also utilize a portable, ergonomically constructed main operating unit (MOU), which may be worn by the patient, and which provides control signals to the ultrasonic transducer(s). An example of a suitable MOU is that described in U.S. Pat. No. 5,556,372 to Talish et al. which is incorporated herein by reference.

Turning to the figures, in particular FIG. 1, one embodiment of the portable ultrasonic treatment apparatus 10 useful in accordance with the invention is shown. The ultrasonic treatment apparatus 10 includes a MOU 12, a placement module 14, and ultrasonic transducer assembly or treatment head 16.

The placement module 14 comprises a placement support 20 which includes at least two or three channels 22 each having an extension 24 mounted therein. Each extension has a transducer pocket 26 at one end or holding one ultrasonic transducer assembly 16. It is contemplated for each extension 24 to have several range of movements besides longitudinal motion, such as articulating to the longitudinal motion.

Figure 2A:
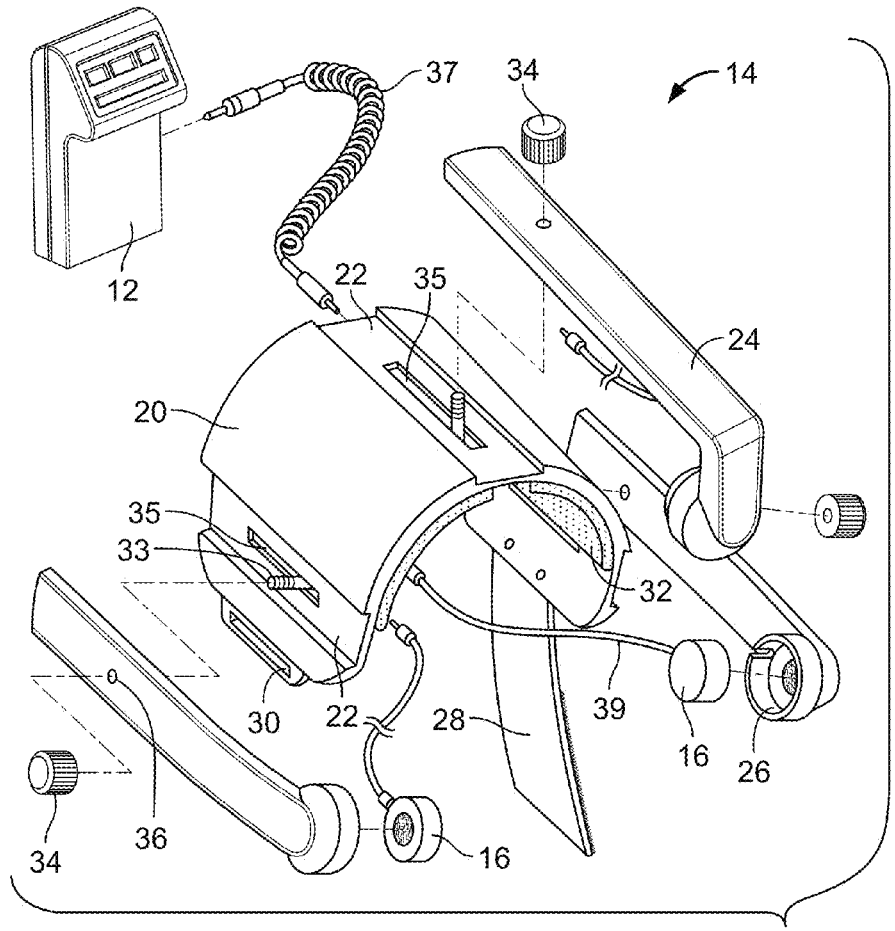
FIG. 2A is an exploded view of the placement module of the portable ultrasonic treatment apparatus illustrated by FIG. 1.
Figure 2B:
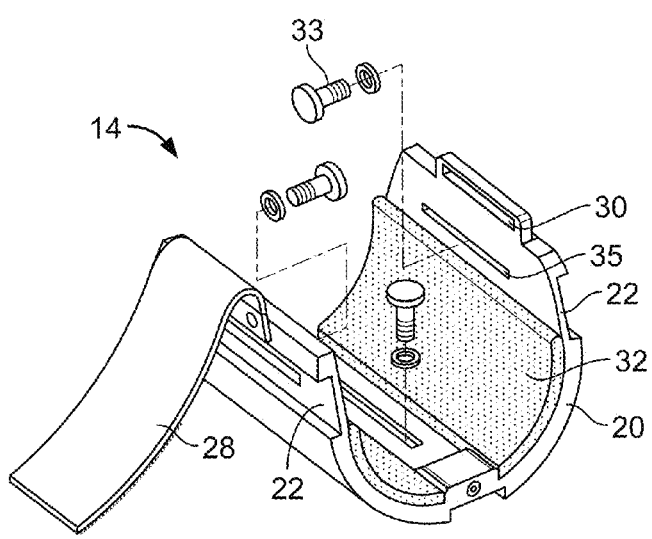
FIG. 2B is a rear underside view of the placement module of the portable ultrasonic treatment apparatus illustrated by FIG. 1.

The placement module 14 further includes a placement band 28 cooperating with slot 30 for securing the placement support 20 to the patient. The placement band 28 is configured to firmly secure the placement module 14 to the patient. A sponge-like material 32 can be used to line the inner surface of the placement support 20 for providing comfort to the patient (FIGS. 2A and 2B). The placement support 20 may be constructed of hard plastics which may be custom molded for a particular body part of the patient.

With reference to FIGS. 2A and 2B, the extensions 24 are mounted to the placement support 20 via screws 33 and thumb screws 34. The screws 33 are passed through slots 35 and holes 36 on the extensions 24 and are threaded to the thumb screws 34. The extensions 24 can be moved to different positions to accommodate patients of all sizes by unthreading the thumb screws 34 and shifting the screws 33 along the slots 35 and threading the screws 33 to the thumb screws 34 at the new position.

The transducer assembly 16 may include circuitry, schematically illustrated by FIGS. 4 and 4A and described below, for exciting the least one transducer therein and is coupled to the MOU by cable 37 and wires 39. The wires 39 are coupled to the placement support 20. The cable 3 is preferably a multiconductor cable capable of transmitting relatively low frequency RF or optical signals, as well as digital signals. The cable 37 may include coaxial cable or other types of suitable shielded cable. Alternatively, the cable 37 may include fiber optic cable for transmitting optical signals. The signals may be transmitted continuously or as a series of pulses.

Figure 3:
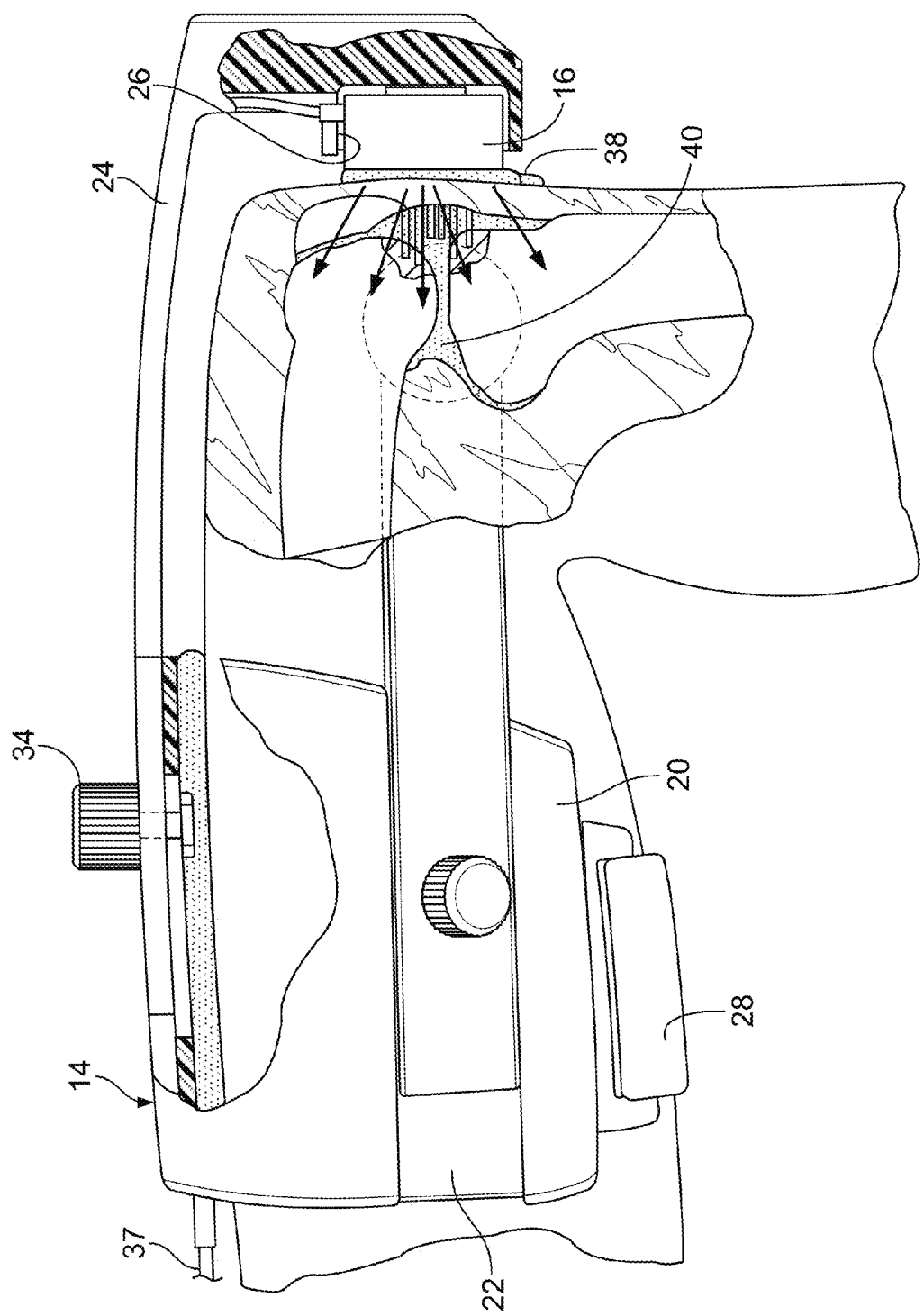
FIG. 3 is a cross-sectional view illustrating a transducer assembly according to one embodiment of the invention impinging ultrasonic waves to connective tissue within the knee, with an ultrasonic conducting gel positioned between the transducer assembly and the patient's knee.

In operation, the placement module 14 is positioned and secured to the patient's body as shown by FIG. 3, such that each transducer assembly 16 lies over the treatment site. A locating ring such as the one disclosed in U.S. patent application Ser. No. 08/389,148, incorporated herein by reference, may be used for determining the location of injured bone, if the patient desires to have one of the transducer assemblies overlying a bone injury, before the placement module 14 is secured to the patient. Once the placement module 14 is properly positioned, the transducer within the transducer assembly 16 is excited for a predetermined amount of time. An ultrasound conducting gel 38 is positioned between the transducer assembly 16 and the injured part of the patient's body to prevent attenuation of the ultrasonic waves as they travel to the connective tissue 40, as shown by FIG. 3.

It is also contemplated that one or more transducers can be converted to receive reflected diagnostic data from the treatment site. This permits real time evaluation of the injury site and healing process.

Figure 4:
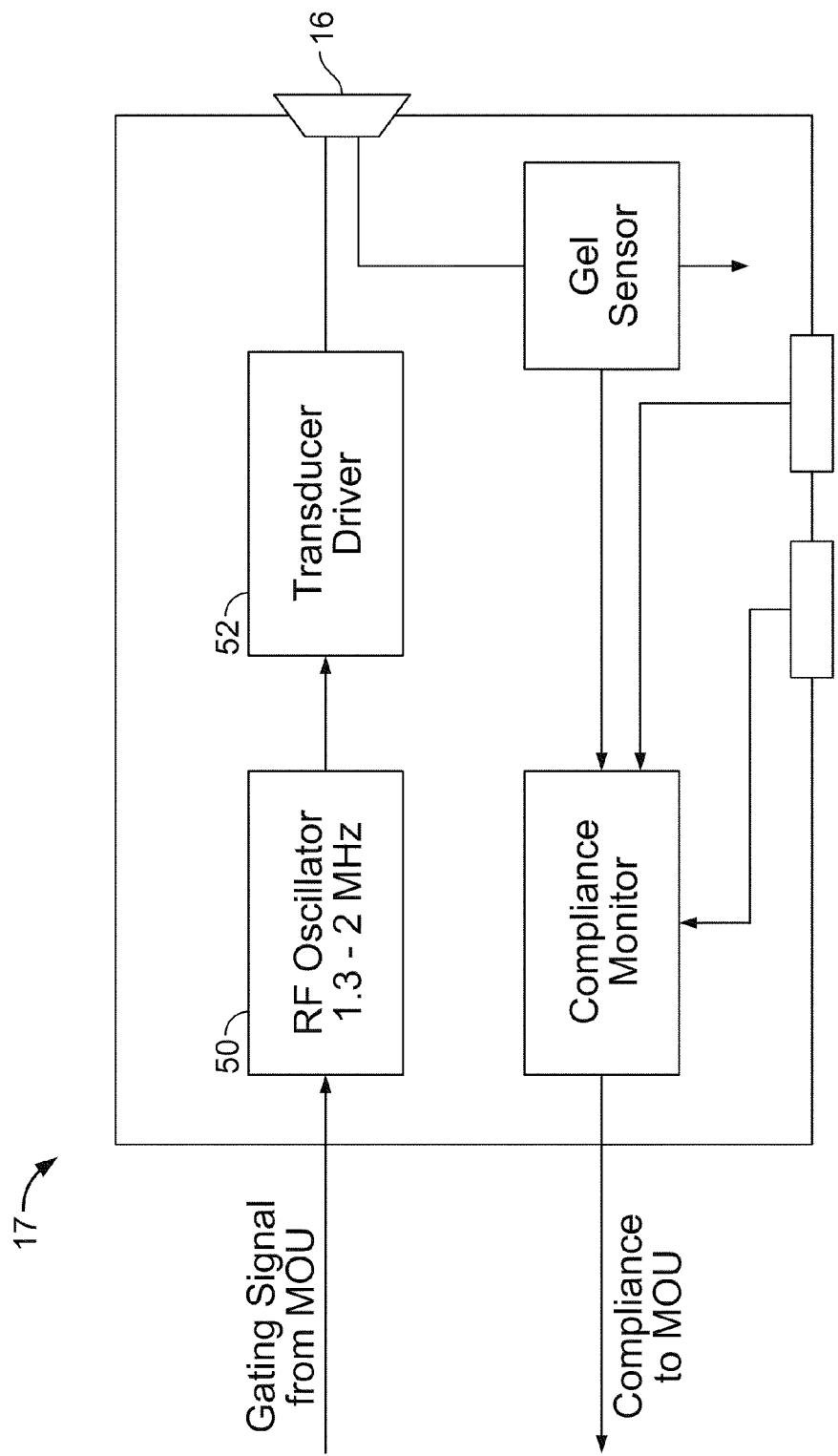
FIG. 4 is a block diagram of one embodiment of the circuitry for one embodiment of an ultrasonic transducer assembly.
Figure 4A:
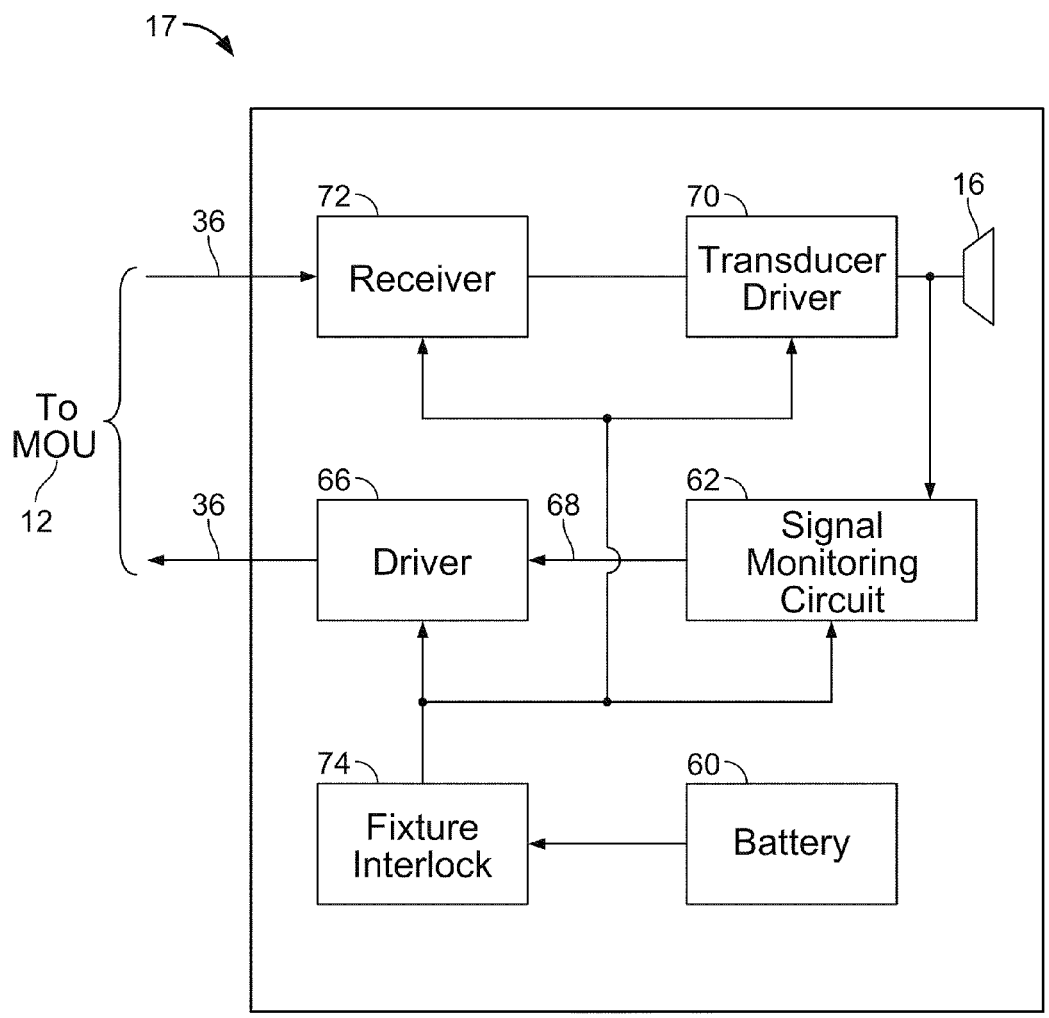
FIG. 4A is a block diagram of an alternative embodiment of the circuitry for the ultrasonic transducer assembly.

With reference to FIG. 4, a block diagram of one embodiment of the ultrasonic transducer assembly circuitry is shown. The transducer assembly circuitry 17 includes a receiver/RF oscillator 50 which receives the signals transferred by a signal generator within MOU 12 via cable 37. The receiver/RF oscillator 50 is connected to transducer driver 52 which excites transducer 16. An alternative embodiment of the transducer assembly circuitry 17 is shown in FIG. 4A. In this embodiment, the ultrasonic transducer assembly 16 includes an internal battery 60 which supplies power to the components within the transducer assembly 16. For example, battery 60 supplies power to signal monitoring circuit 62 and signal driver 66. The signal monitoring circuit 62 provides, preferably, a digital output signal 68 which represents the waveform characteristics of the output of transducer driver 70. These characteristics can be displayed on a digital display and may include, for example, the frequency, pulse repetition frequency, the pulse width and the average output power of the transducer 16. The output signal 68 of signal monitoring circuit 62 is transferred to the signal generator within MOU 12 via driver 66 and cable 37. The signal generator may include a processor and a switch for regulating the signal characteristics. Control signals from the MOU 12 are received by receiver 72 via cable 37. Safety or fixture interlock 74, which may include switches on the outer surface of the placement module 14 or transducer assembly 16, ensures that the placement module 14 is properly positioned before providing power to the internal components of the transducer assembly 16.

Figure 5:
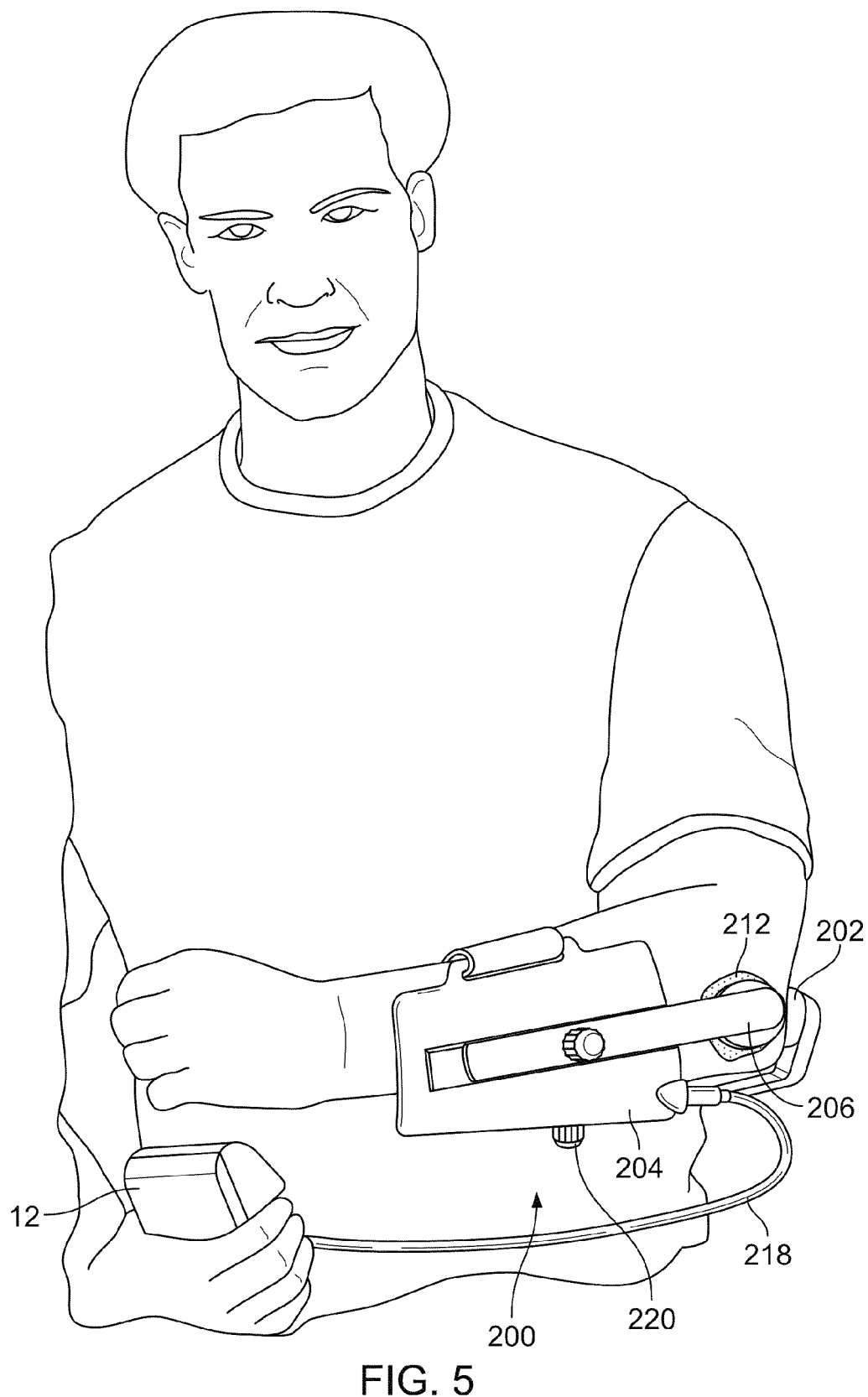
FIG. 5 is a perspective view of a second embodiment of the portable ultrasonic treatment apparatus, illustrating a main operating unit controller and a placement module for treating connective tissue injuries or pathologies within the elbow region.

A second embodiment of the portable ultrasonic treatment apparatus of the present invention is illustrated by FIG. 5 and designated generally by reference numeral 200. The treatment apparatus 200 includes MOU 12 and transducer assemblies 202 affixed to a placement module 204 via extensions 206 for ultrasonically stimulating the repair or healing of tissue in the elbow region. Each transducer assembly 202 includes a power transducer 212 connected to the MOU 12 by cable 218. An ultrasonic conducting gel 212 is positioned between the transducer assemblies 202 and the treatment site to prevent attenuation of the ultrasonic waves as they travel to the tissue being treated. In order to accommodate various patients, the extensions 206 can be adjusted to several positions by unthreading thumb screws 220. The circuitry for each transducer assembly 202 may be similar to that disclosed for the first embodiment and schematically illustrated by FIGS. 4 and 4A.

It is envisioned that the placement module 204 b constructed from suitable conductive plastics, such as conductive ABS plastics with either carbon, stainless steel, nickel or aluminum fibers to forego the use of wires for connecting the transducer assemblies 202 to the cable 218. In such an embodiment, the conductive placement module 204 would be used to electrically connect the transducer assemblies 202 to the MOU 12 via cable 218.

Figure 6:
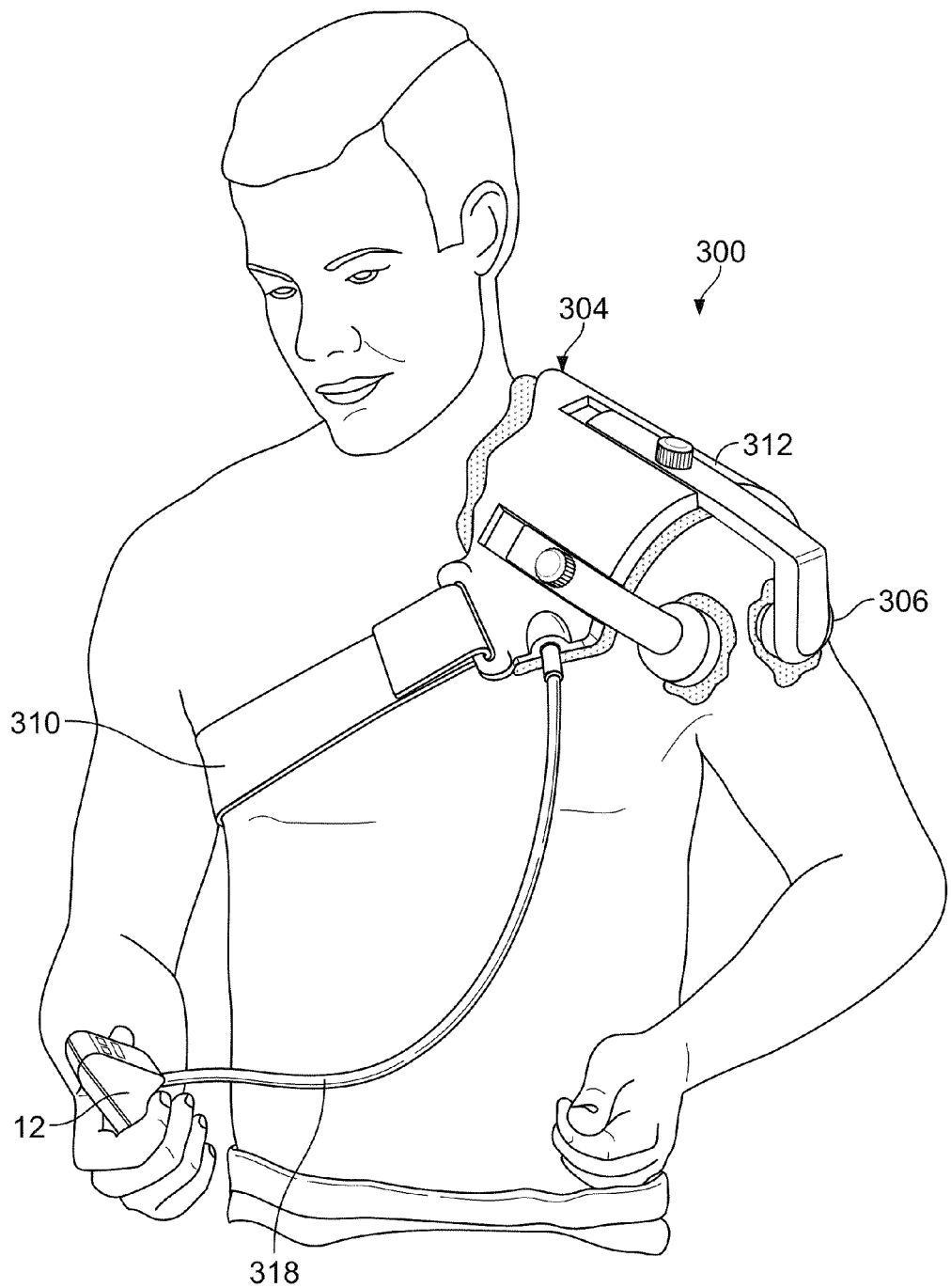
FIG. 6 is a perspective view of a third embodiment of the portable ultrasonic treatment apparatus, illustrating a main operating unit controller and a placement module for treating connective tissue injuries or pathologies within the shoulder region.

With reference to FIG. 6, a third embodiment of the portable ultrasonic treatment apparatus of the present invention is illustrated. In this embodiment, the treatment apparatus 300 includes a MOU 12, a placement module 304, and ultrasonic transducer assemblies 306. The placement module 304 is configured for placement on the shoulder region and includes a placement band 310 and a placement support 312. Each transducer assembly 306 is connected to the MOU 12 by cable 318 to power transducer assembly circuit within each assembly 306. The circuitry (not shown) may be similar to that disclosed for the first and second embodiments and schematically illustrated by FIGS. 4 and 4A.

In operation, transducers within transducer assemblies 306 are excited for a pre-determined period of time to impinge ultrasonic waves to articular cartilage within the shoulder region.

Figure 7:
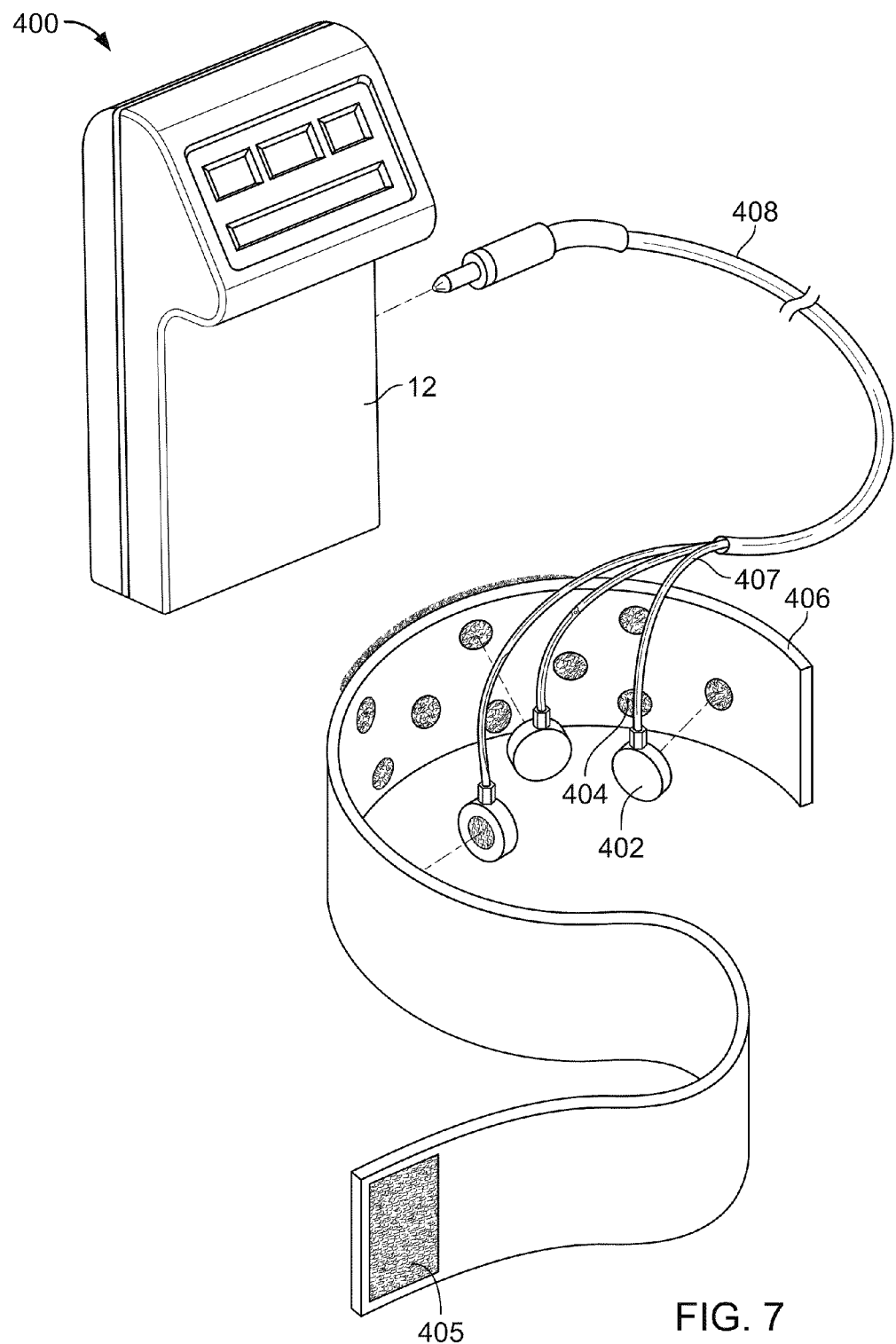
FIG. 7 is a perspective view of a fourth embodiment of the portable ultrasonic treatment apparatus illustrating a main operating unit controller and a placement module.
Figure 8:
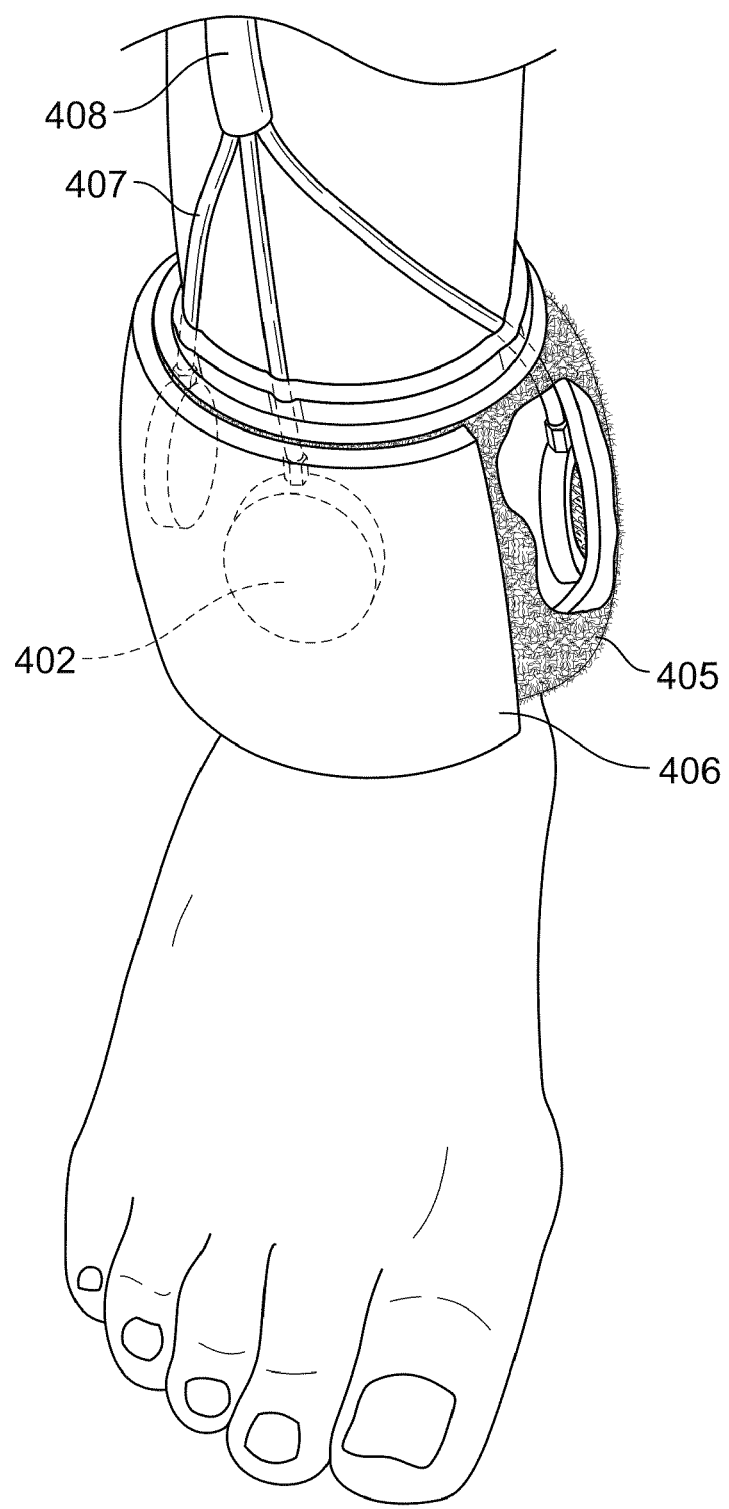
FIG. 8 is a perspective view of the portable ultrasonic treatment apparatus illustrated by FIG. 7 mounted on a patient's ankle.

A fourth embodiment of the portable ultrasonic treatment apparatus of the present invention which is primarily suitable for the treatment of connective tissue is illustrated by FIGS. 7 and 8. In this embodiment, the apparatus 400 includes at least one ultrasonic transducer assembly 402 positioned within pockets 404 on a strip 406. The transducer assemblies 402 may be arranged in a plurality of configurations within pockets 404 to accommodate many patients' anatomical differences. The strip 406 is secured in proximity to the desired treatment site as shown by FIG. 8 by a self-tieing material 405. The strip 406 is connected is wires 407 and cable 408 to a MOU 12 which contains circuitry for exciting the at least one ultrasonic transducer assembly 402 affixed to the strip 406.

In operation, at least one transducer assembly 402 is excited to impinge ultrasonic waves to the treatment site as shown by FIG. 8. It is contemplated that during treatment an ultrasonic conducting gel is positioned between the strip 406 and the patient's body to prevent attenuation of the ultrasonic waves.

It is also contemplated to manufacture the strip 406 from suitable conductive plastics such as conductive, ABS plastics with either carbon, stainless steel, nickel or aluminum fibers to forego the use of wires for electrically connecting the at least one ultrasonic transducer 402 to the cable 408.

Figure 9:
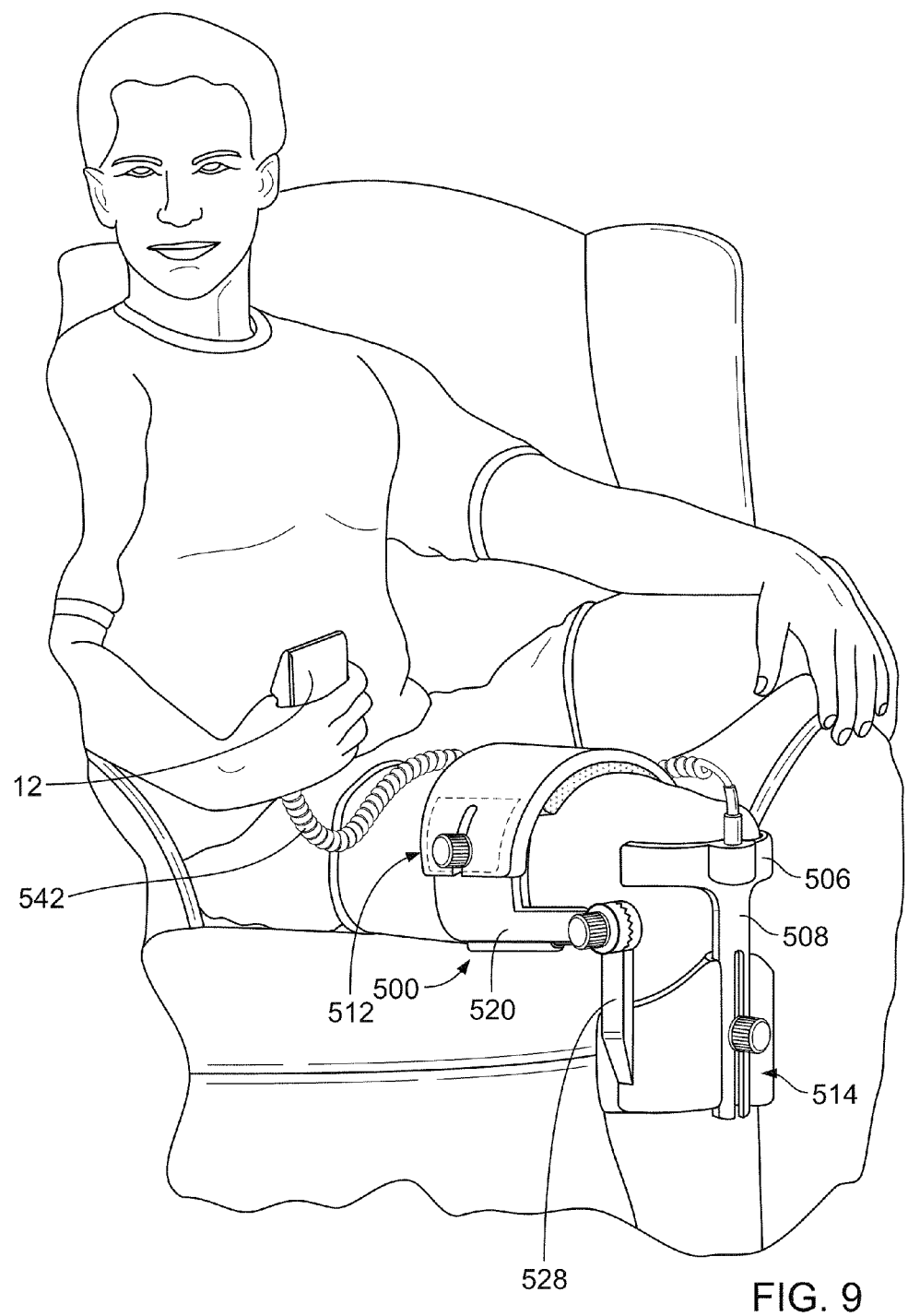
FIG. 9 is a perspective view of a fifth embodiment of the portable ultrasonic treatment apparatus, illustrating a main operating unit or controller and a placement module for treating connective tissue injuries or pathologies within the knee region.
Figure 10A:
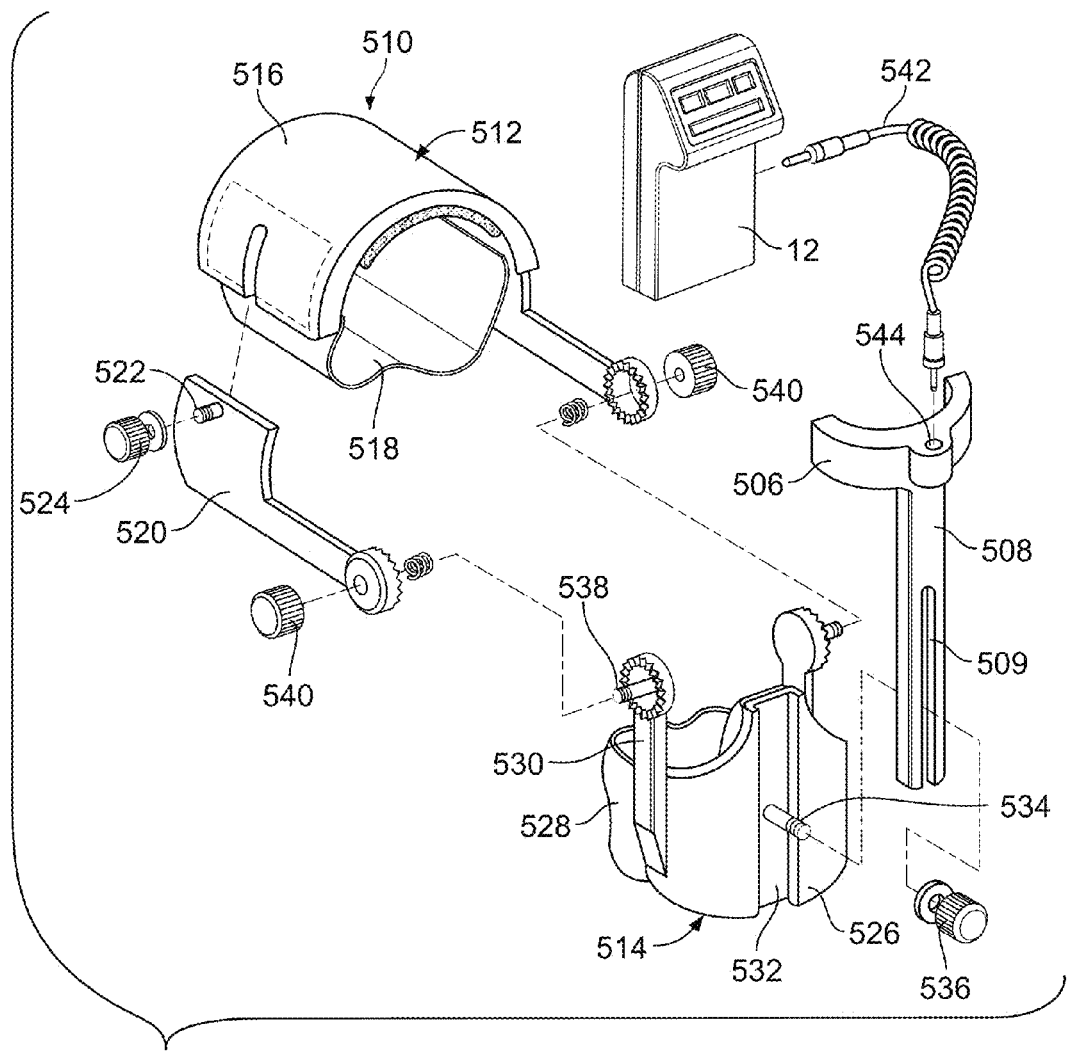
FIG. 10A is an exploded view of the portable ultrasonic treatment apparatus illustrated by FIG. 9.
Figure 10B:
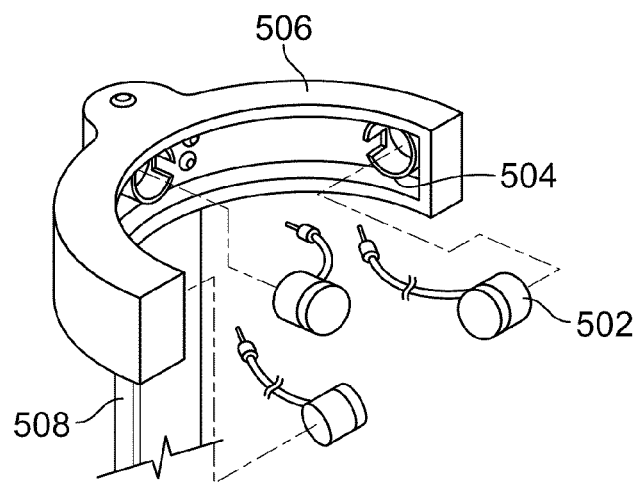
FIG. 10B is a perspective view of a support member of the portable ultrasonic treatment apparatus illustrated by FIG. 9.

A fifth embodiment of the portable ultrasonic treatment apparatus of the present invention which is primarily suitable for the treatment of connective tissue is illustrated by FIGS. 9-10B. In this embodiment, the apparatus 500 includes a MOU 12 and three ultrasonic transducer assemblies 502 positioned within pockets 504 on an inner surface of a concave plate 506 as shown by FIG. 10B. The concave plate 506 is positioned at one end 30 of a vertical bar 508 having a slot 509 at a lower portion. The apparatus 500 further includes a locking support module 510 having a thigh support 512 and a leg support 514.

As shown by the exploded view of FIG. 10A, the high support 512 includes a thigh support plate 516, a securing band 518, and two horizontal locking extensions 520 affixed to the thigh support plate 516 by crews 522 and thumb screws 524. The leg support 514 includes a leg support late 526, a securing band 528, and two vertical locking extensions 530 affixed to the leg support plate 526. The vertical bar 508 is configured to mount within a channel 532 on the leg support 514. The vertical bar 508 is secured to the channel 532 by screw 534 and thumb screw 536. The vertical bar 508 can be moved vertically along the channel 53 by unthreading the thumb screw 536 to accommodate various patients.

The thigh support 512 and the leg support 514 are locked to each other by locking the horizontal locking extensions 520 and the vertical locking extensions 530 by screws 538 and thumb screws 540 to prevent the patient from moving the thigh with respect to the leg during treatment and to ensure that the transducer assemblies 502 remain fixed in their proper positions. The transducer assemblies 502 are connected via a cable 542 which is plugged in to hole 544 to the MOU 12 which contains circuitry for exciting the ultrasonic transducer assemblies 502. It is contemplated that during treatment an ultrasonic conducting gel is positioned between the transducers 502 mounted in concave plate 506 and the patient's body to prevent attenuation of the ultrasonic waves.

Alternative embodiments of the placement module described above also form a part of the invention, and are illustrated in FIG. 11-19. These embodiments of placement module generally contain a covering member, which covers or surrounds a part of the joint or associated limbs or other adjacent anatomical structures, and provides attachment points for ultrasonic transducers or assemblies containing ultrasonic transducers. The covering member, while adjustable, is intended to remain in a fixed position once disposed on or around the joint, and its attachment points provide a frame of reference for appropriately positioning the ultrasonic transducer or assembly to direct the ultrasound toward the treatment site. While the embodiments illustrated herein are specifically adapted for use with the human knee, and more specifically adapted to provide ultrasound therapy to the ACL area, it will be recognized that these embodiments are not so limited in application, and can be readily used or adapted for use with other joints, or to treat other connective tissue within the knee.

Figure 11A:
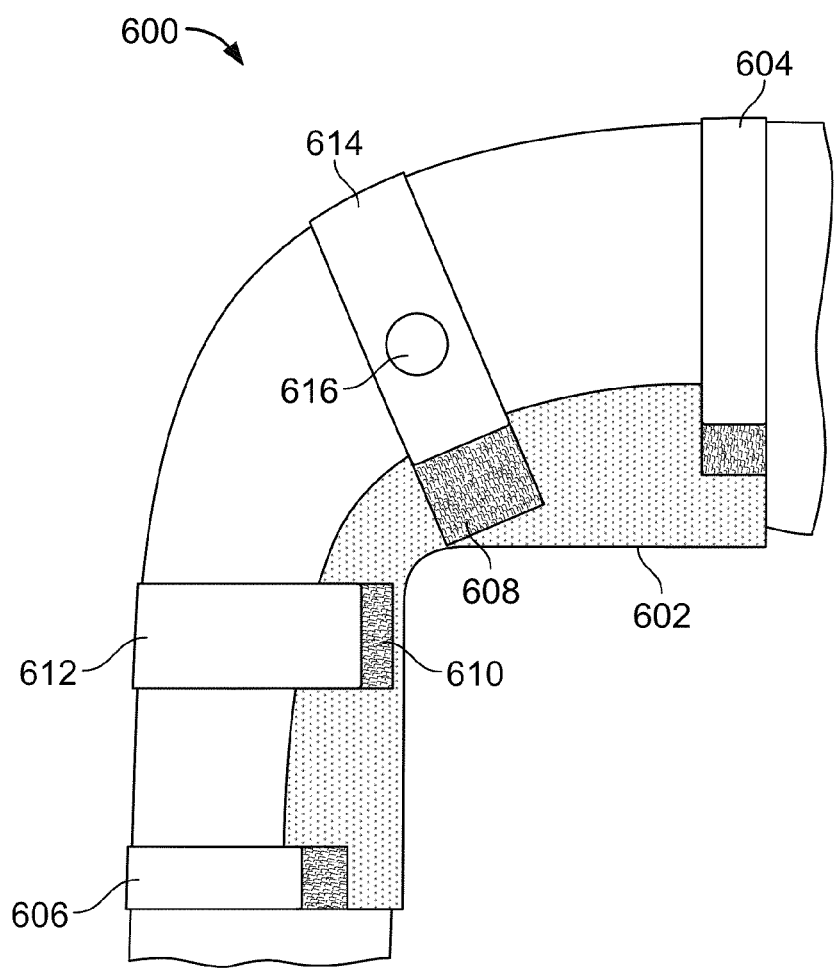
FIG. 11A is a side view of an alternative embodiment of a placement module according to the invention.
Figure 11C:
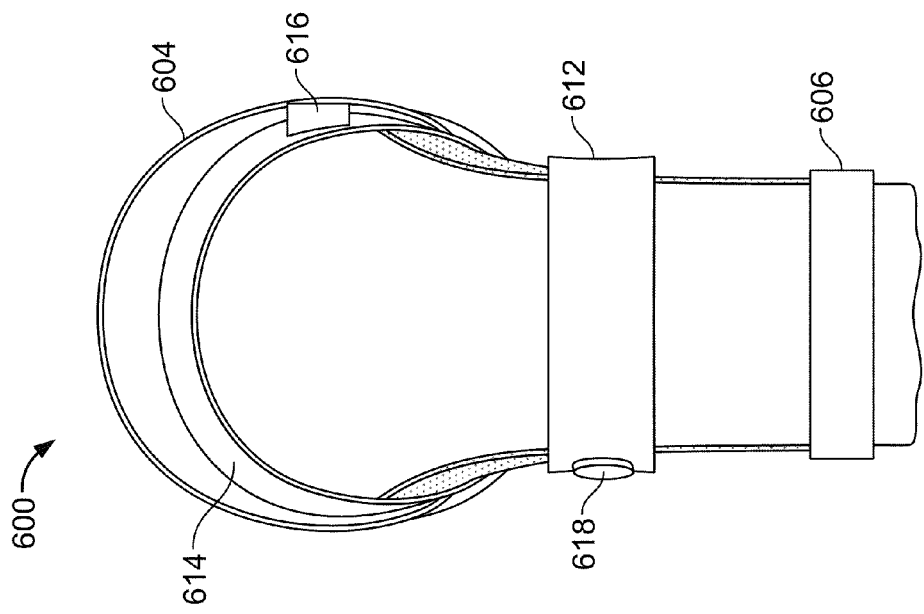
FIG. 11C is a front view of the placement module of FIGS. 11A and 11B.
Figure 11B:
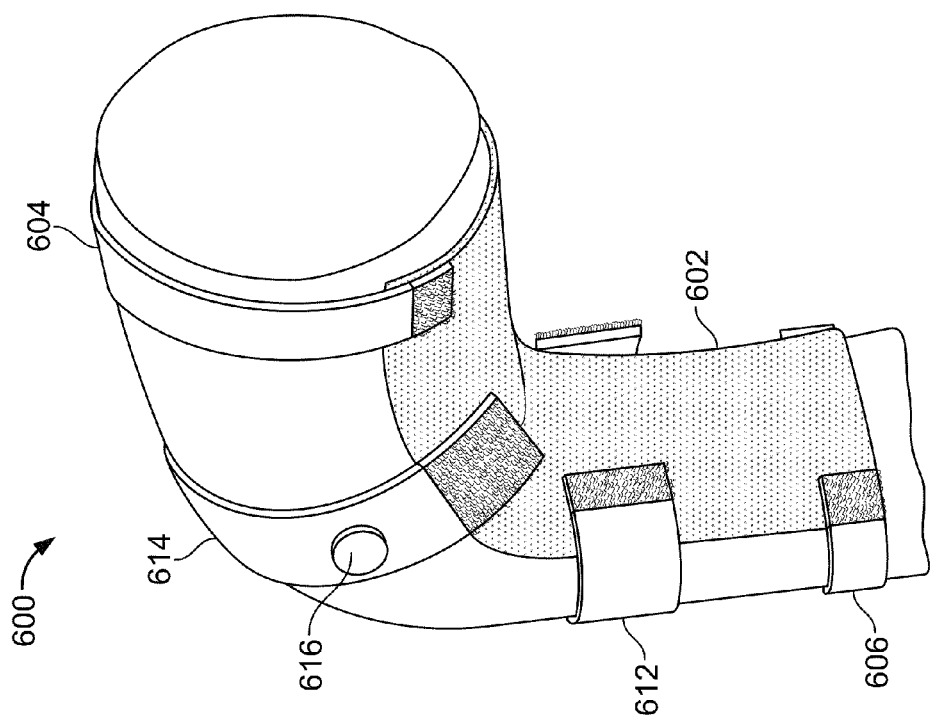
FIG. 11B is a rear perspective view of the placement module of FIG. 11A.

FIGS. 11A, 11B, and 11C illustrate an embodiment of placement module 600 having covering member 602 secured to the underside of the knee by upper and lower securing straps 604 and 606, respectively. Covering member 602, which may be flexible (e.g., a fabric) or rigid (e.g., a plastic) contains receiving areas 608, 610, which are adapted to receive ultrasonic transducer assemblies 612, 614. These are illustrated as straps containing ultrasonic transducer ports 616, 618, and which can be secured to covering member 602 by hook-and-loop fabric (e.g., VELCRO). As used herein, the term "ultrasonic transducer assembly" means an assembly capable of receiving and holding an ultrasonic transducer, with or without the transducer attached thereto. By positioning the transducer assemblies properly at their attachment points on the covering member, the ultrasonic transducers will be appropriately positioned to direct ultrasound to the area of the surgery or discomfort.

Figure 12A:
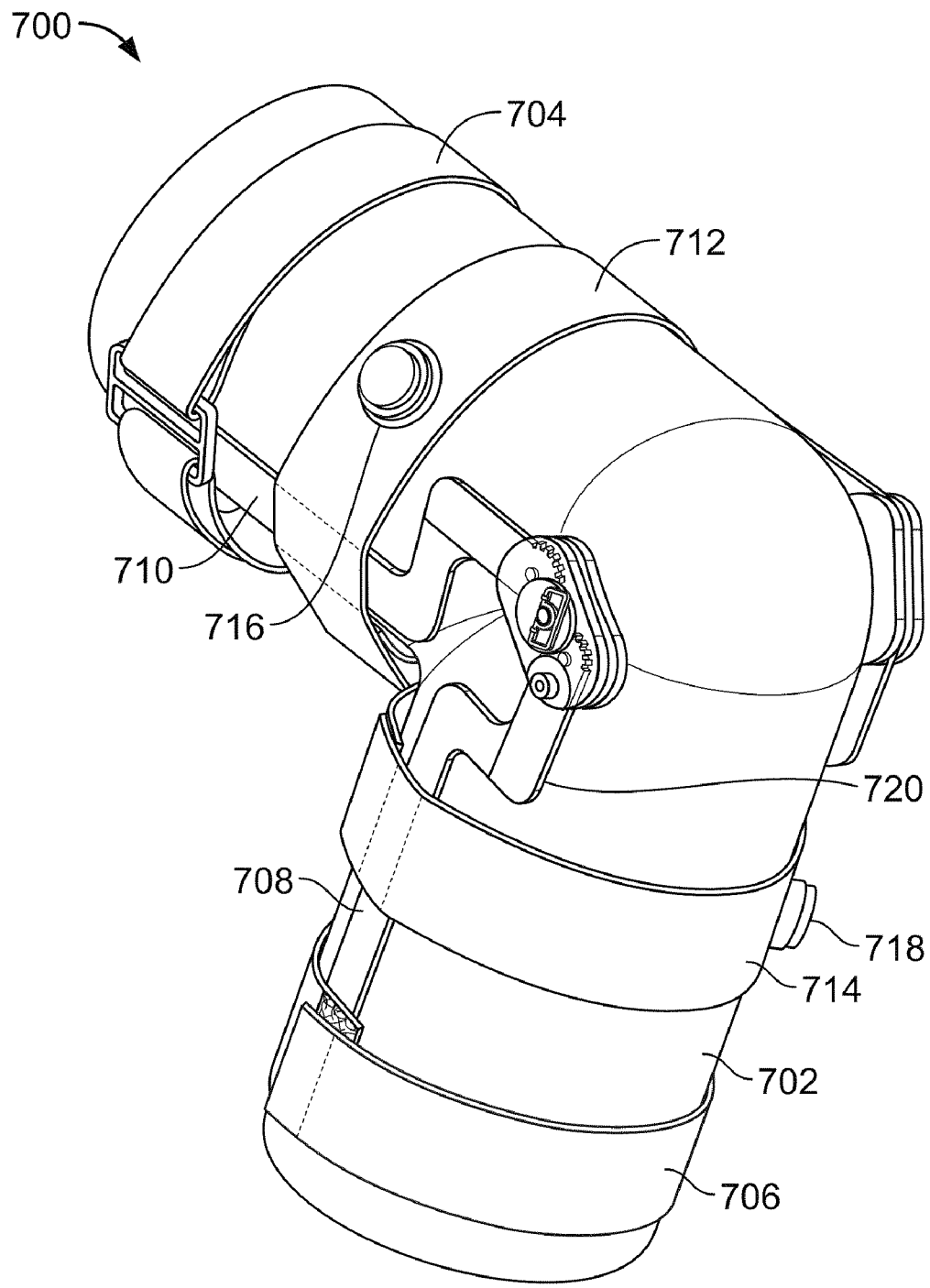
FIG. 12A is a left perspective view of another alternative embodiment of a placement module according to the invention.
Figure 12B:
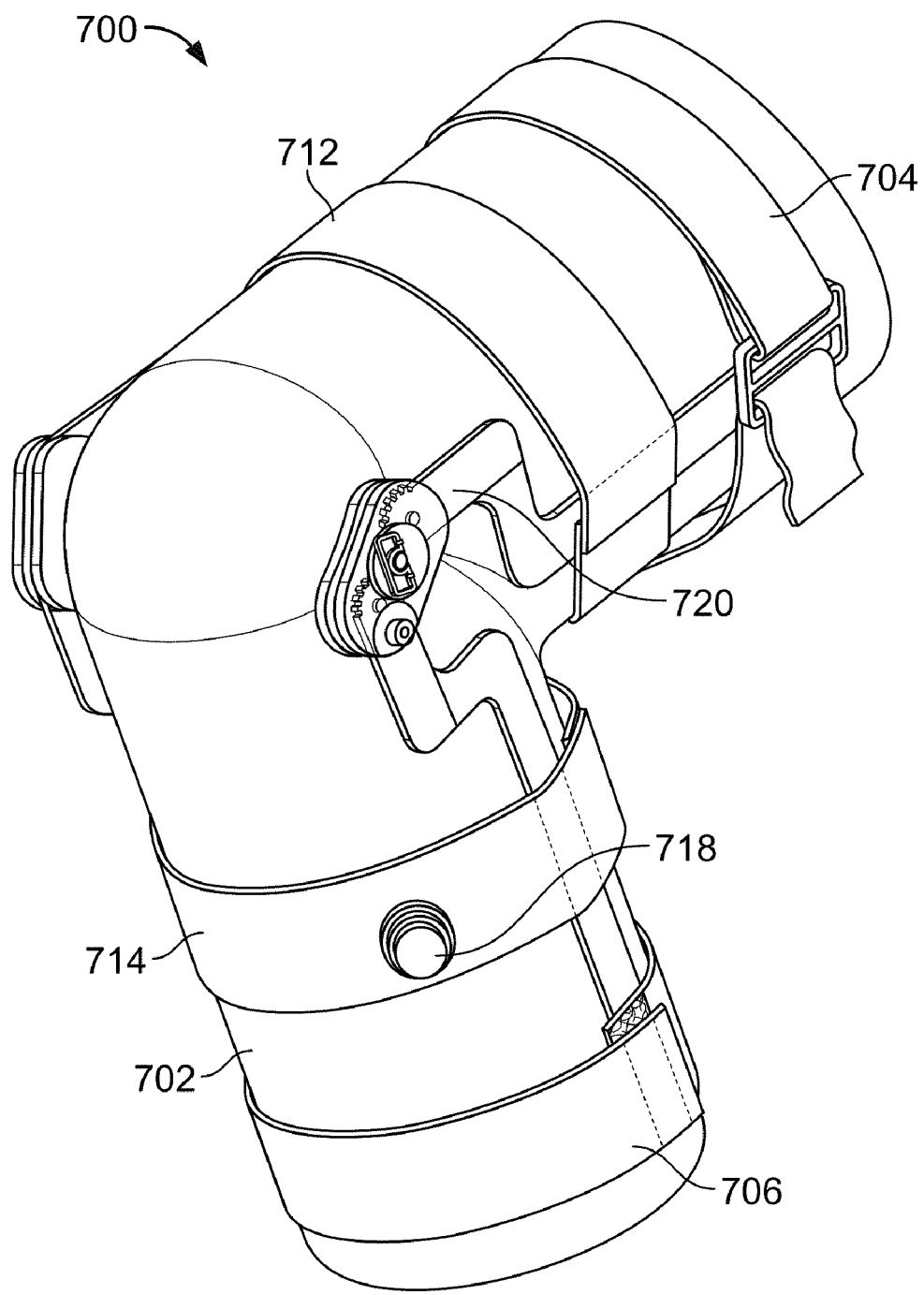
FIG. 12B is a right perspective view of the placement module illustrated in FIG. 12A.
Figure 12C:
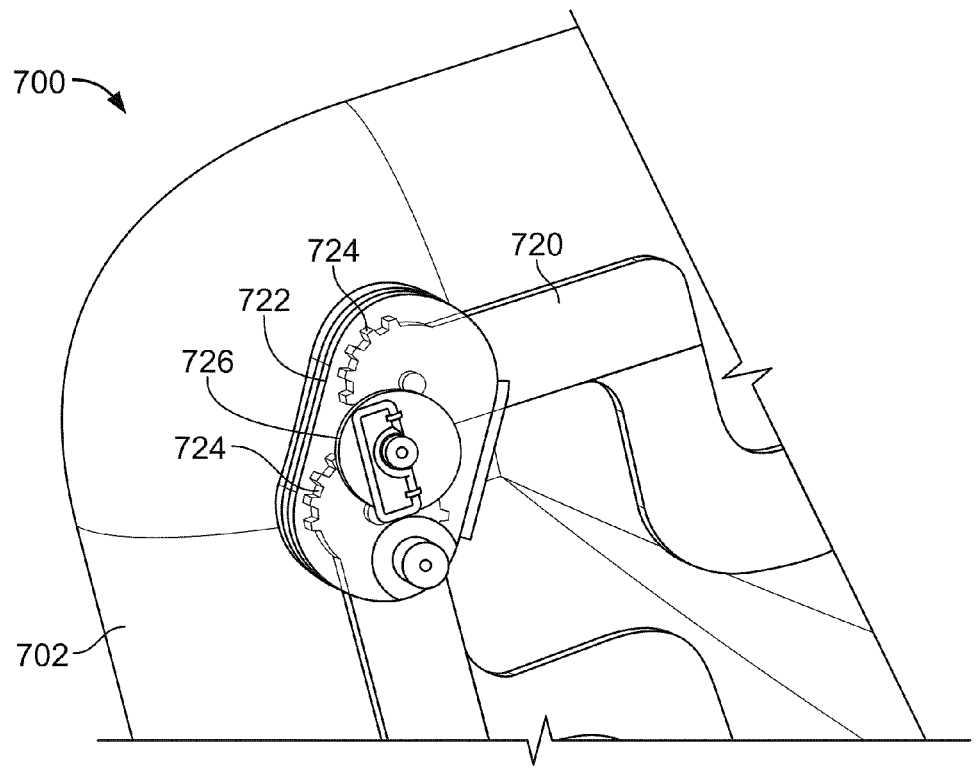
FIG. 12C is an expanded perspective view of the placement module illustrated in FIGS. 12A and 12B.
Figure 12D:
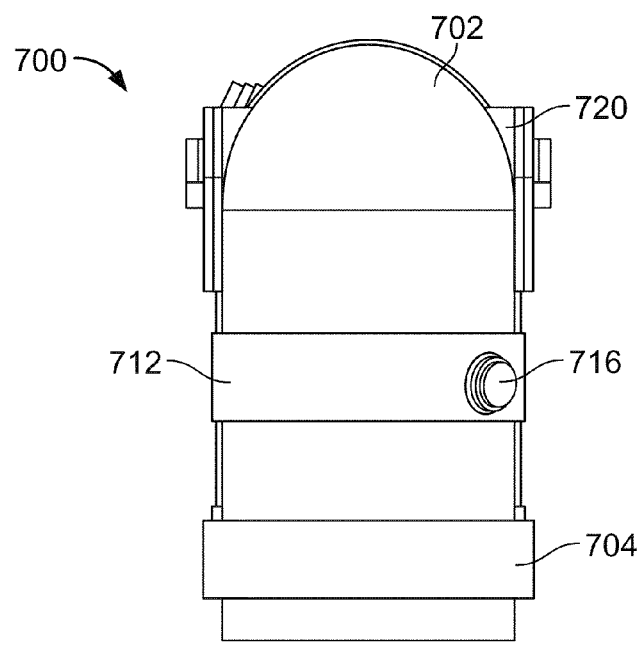
FIG. 12D is a top view of the placement module illustrated in FIG. 12A through 12C.

FIGS. 12A, 12B, 12C, and 12D illustrate another embodiment of placement module 700 according to the invention. Covering member 702, which may be either rigid or flexible covers the front of the knee, and is secured to the legs by straps 704 and 706. Covering member 702 contains receiving areas 708, 710, which are adapted to receive ultrasonic transducer assemblies 712, 714, which contain ultrasonic transducer ports 716, 718. In the embodiment illustrated, placement module 700 also contains rigid strut 720, which adjusts to hold the joint in a predetermined position. As best seen in FIG. 12C, rigid strut 720 can be provided with adjustability by locking hinge or pivot 722, which is fitted with lockout gears 724, as well as with optional D-ring 726, which allows for the use of an optional strap for added security or an additional ultrasonic transducer assembly. As with the placement module illustrated in FIG. 11, the ultrasonic transducer assemblies 712, 714 are straps that, like the securing straps 704, 706 are secured to the covering member with hook and loop closures.

Figure 13B:
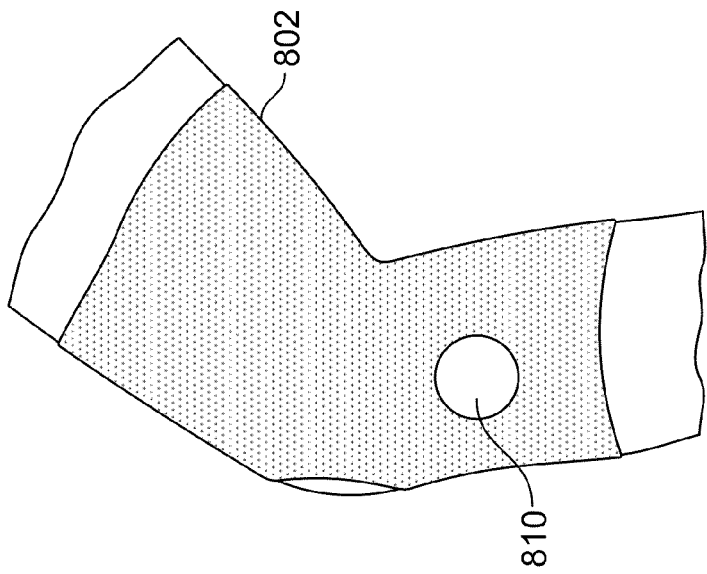
FIG. 13B is a right perspective view of the placement module illustrated in FIG. 13A.
Figure 13A:
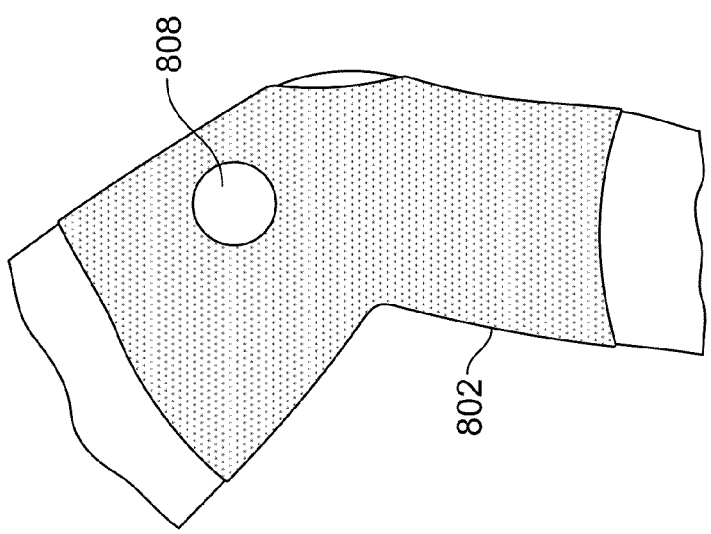
FIG. 13A is a left perspective view of another alternative embodiment of a placement module according to the invention.

FIGS. 13A and 13B illustrate yet another embodiment of placement module 800 having covering member 802, made from a flexible, elastic fabric that surrounds the knee and surrounding portions of the leg. Receiving areas 808, 810 are disposed in the fabric itself, so that an ultrasonic transducer can be inserted directly therein. The elastic material holds the transducers in position and directs the ultrasound toward the ACL treatment site.

Figure 14A:
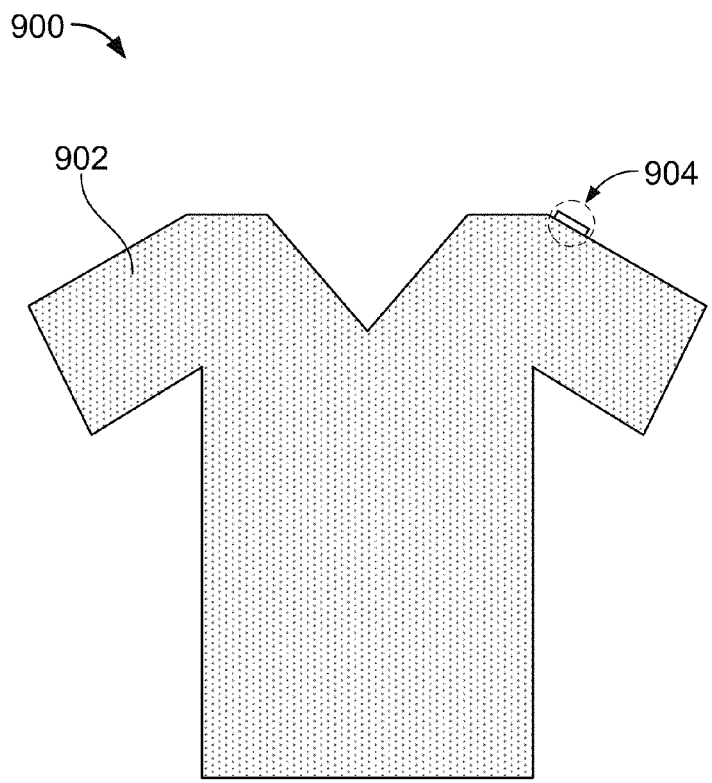
FIG. 14A is a schematic view of a placement module adapted to cover the torso area.
Figure 14B:
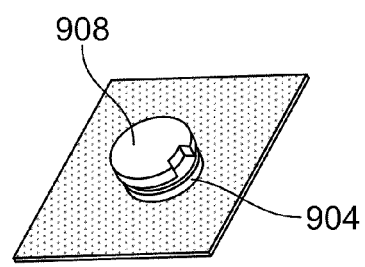
FIGS. 14B and 14C are close up schematic views of open (14B) and closed (14C) transducer ports.
Figure 14C:
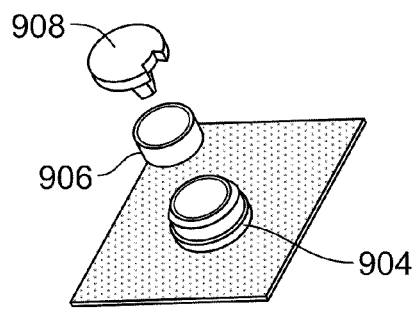

FIG. 14A illustrates another embodiment of placement module 900, illustrated as a fabric shirt (forming covering member) 902 that can be worn over the torso. The shirt has a transducer port 904 (one is illustrated, but multiple ports may be present). FIG. 14B is a schematic diagram showing a close-up view of transducer port 904, wherein transducer port cap 908 is in the closed position. FIG. 14C is a schematic diagram showing transducer port cap 908 in the open position, so that transducer 906 is visible (similar ports can be used with the embodiments shown in the other figures). The covering member or fabric shirt 902 can be made from an elastic or stretchable fabric, such as Spandex or the like, to hold the transducer port next to the skin of the patient.

Figure 15A:
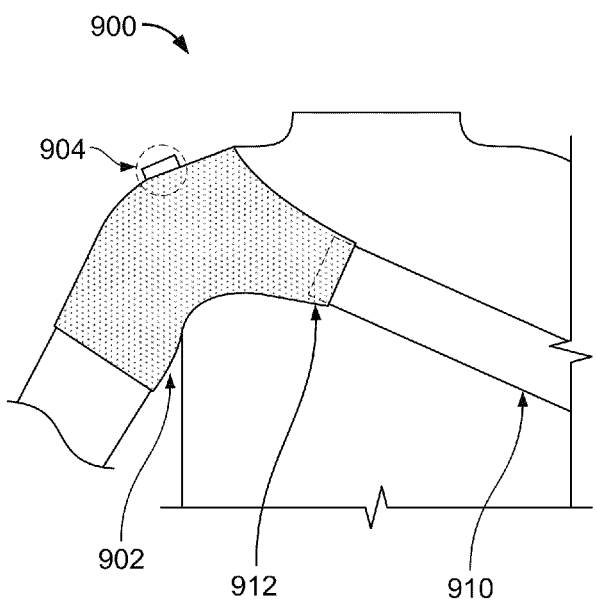
FIG. 15A shows a schematic view of another embodiment of the placement module of the invention in the form of an adjustable shoulder brace.
Figure 15B:
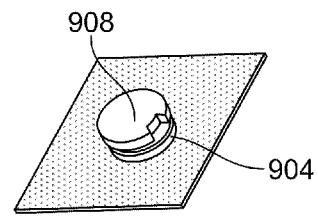
FIGS. 15B and 15C are close up schematic views of open (15B) and closed (15C) transducer ports.
Figure 15C:
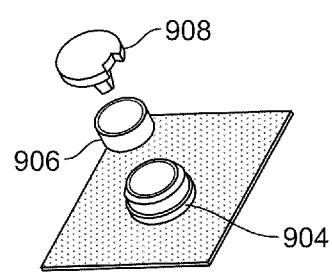

FIG. 15A illustrates another embodiment of placement module 900 in the form of an adjustable shoulder brace. Covering member 902 can be made of an elastic or stretchable material to hold transducer port 904 firmly against the skin. Covering member 902 can be secured in place by retaining strap 910, which can be disposed around the torso and secured via one or more attachment point, 912. Retaining strap 910 and covering member 902 may form an integral piece that wraps around the body, or may be formed from two separate pieces of fabric having two attachment points. As with the embodiment shown in FIG. 14, the shoulder brace shown in FIG. 15A is well adapted to provide ultrasonic treatment to connective tissue in the shoulder area. The embodiment of transducer assembly or port 904 illustrated in FIG. 15B and FIG. 15C is described above with respect to FIG. 14B and FIG. 14C.

Figure 16:
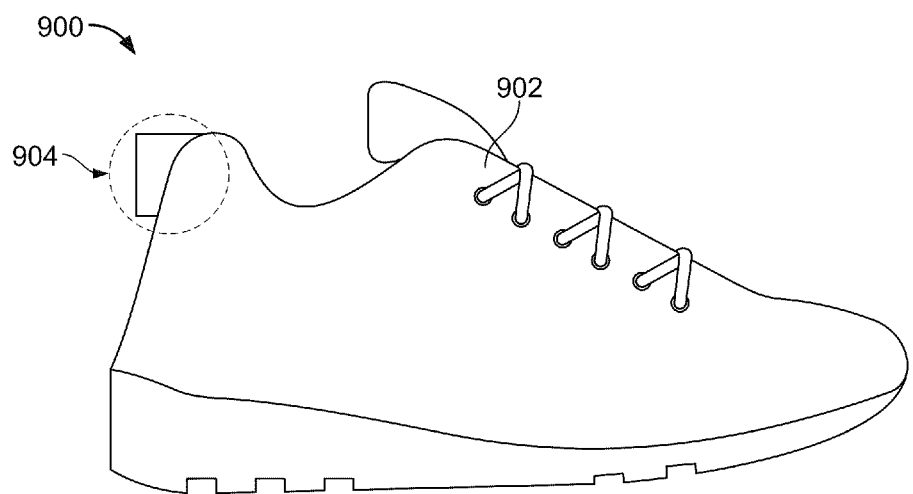
FIG. 16 is a schematic view illustrating an embodiment of the placement module of the invention, wherein the covering member is a shoe or sneaker.

FIG. 16 illustrates an embodiment of placement module 900, wherein the covering member 902 is a shoe or sneaker having transducer assembly or port 904 attached thereto. As illustrated, the placement module 900 is particularly adapted to supply ultrasound to tissue in the area of the ankle, e.g., for repair or healing of Achilles' tendon injuries. However, transducer assembly or port 904 could be readily placed in other areas of the shoe or sneaker to apply ultrasound to other parts of the ankle or foot.

Figures 17A, 17B:
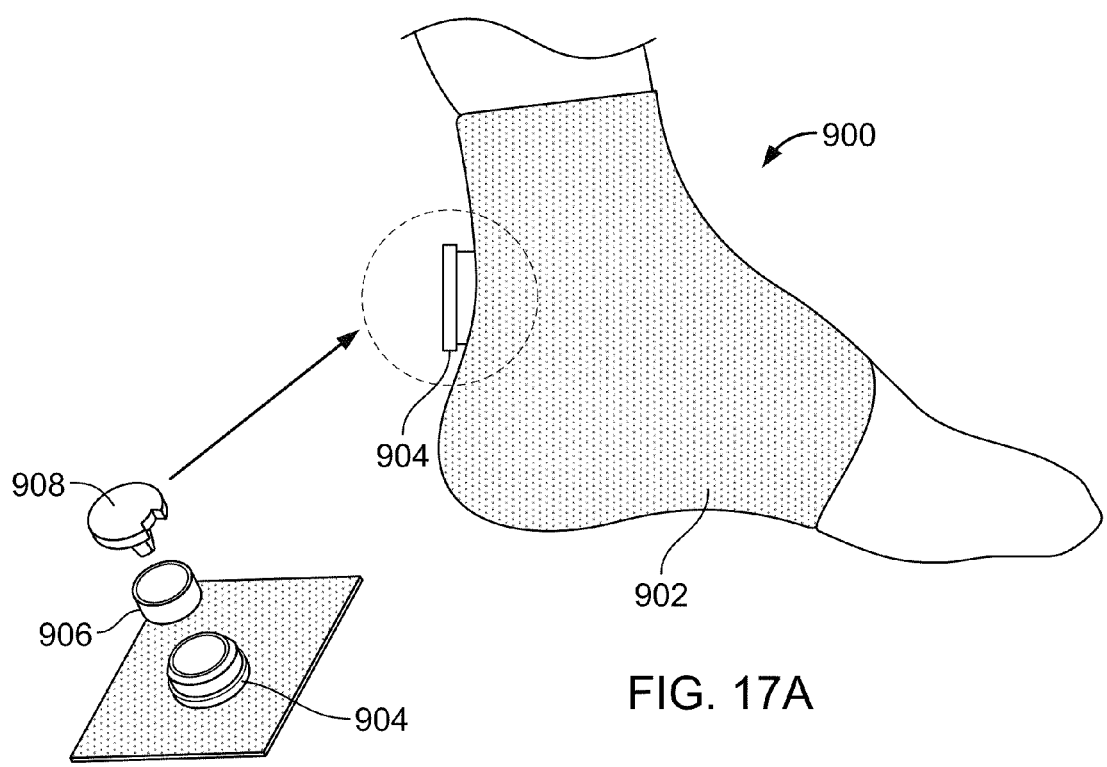
FIG. 17A is a schematic view of another embodiment of a placement module similar in application to that of FIG. 16, but wherein the covering member is an elastic or stretchable.
FIG. 17B is a close up schematic view of the transducer port or assembly.

FIG. 17A illustrates another embodiment of placement module 900, similar in application to that of FIG. 16, but wherein the covering member 902 is an elastic or stretchable fabric holding transducer port or assembly 904 in place firmly against the skin. As with the embodiment shown in FIG. 16, placement of the transducer port or assembly can be varied to apply ultrasound to different tissues in the foot or ankle. The embodiment of transducer assembly or port 904 illustrated in FIG. 17B is described above with respect to FIG. 14C.

FIG. 18A illustrates an embodiment of placement module 900 suitable for application of ultrasound to the wrist or hand area. Covering member 902 forms an adjustable strap that encircles the wrist and holds transducer port or assembly 904 against the skin of the patient. The embodiment of transducer assembly or port 904 illustrated in FIG. 18B is described above with respect to FIG. 14C.

FIG. 19 illustrates an embodiment of placement module 900 suitable for application of ultrasound to the elbow area. Covering member 902 is an elastic or stretchable fabric holding transducer port or assembly 904 in place firmly against the skin. Although illustrated disposed on the outer side of the elbow, the transducer port or assembly 904 can be disposed along the inner surface of the elbow if desired.

EXAMPLE 1

An ovine model of soft tissue graft (digital extensor tendon) reconstruction of the ACL was utilized to allow for assessment of the method and apparatus of the invention. A modified ACL reconstruction was performed on 21 animals in three groups of 7 animals. Control groups of 2 animals (provided with no ultrasound treatment), and experimental groups of animals (provided with ultrasound treatment for 20 minutes continuously each day) were harvested at the end of 3, 6, and 12 weeks.

The right hind limb was operated on in all animals. The anterior cruciate ligament (ACL) was visualized and removed at the insertion site through an antero-medial arthrotomy. The ACL reconstruction was performed using a digital extensor tendon graft. The tendon graft was harvested from the same limb by 2 stab incisions. The graft was whip stitched using # 2 Ethibond and prepared using the Acufex Graftmaster. The graft was doubled and passed through 4.5 mm tunnels in the tibia and femur. Endobutton fixation was used on the femoral side with tibial fixation over a bony post. The surgical incisions were then closed using standard suturing techniques. The animals were then recovered and ultrasound treatment was initiated on the members of the experimental group one day following surgery.

The animals in the treatment groups were treated with pulsed low intensity ultrasound (1.5 MHz, pulsed at 1 KHz, 200 μs burst width) for 20 minutes per day for the duration of the study. Ultrasound devices having two ultrasound transducers were used. One transducer was coupled to the skin (wool was shaved) over the femoral bone tunnel containing the graft, while the other was coupled to the skin over the tibial attachment tunnel. The transducers were held in place during treatment with strapping.

Animals were sacrificed at 3, 6 and 12 weeks following surgery with an intravenous lethal injection of anesthetic. The right hind limb of each was stripped of soft tissue and muscle and fixed in 10% phosphate buffered formalin for a minimum of 72 hours with changes every 24 hours. The femoral and tibial bone tunnels were isolated using a saw and decalcified in 10% formic acid-formalin solution. The femur and tibial tunnels were sectioned into 2-3 mm slices from the joint space to the outer cortex and placed into cassettes for paraffin embedding. Five-micron thick sections were cut on a microtome and stained with hematoxylin and eosin for microscopic analysis.

Figure 20A:
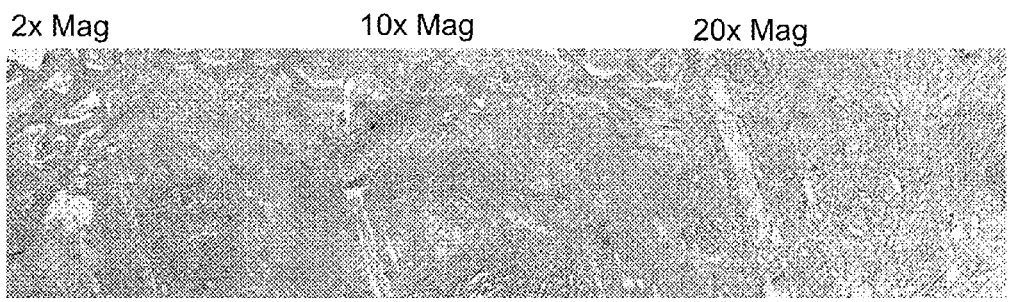
FIG. 20A is a photomicrograph of ovine tendon graft after 3 weeks without treatment according to the invention.
Figure 20B:
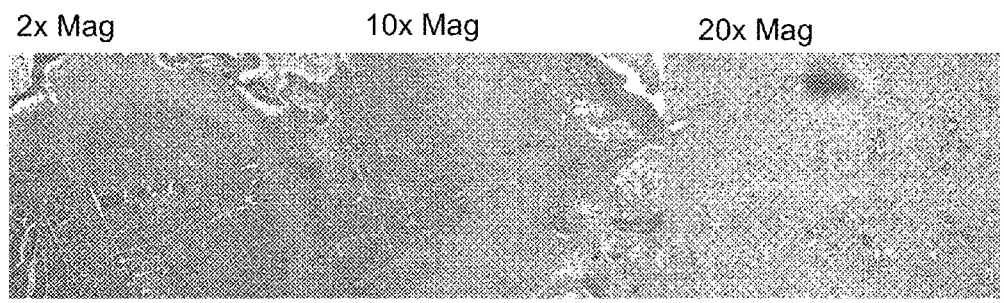
FIG. 20B is a photomicrograph of ovine tendon graft after 3 weeks of ultrasonic treatment according to the invention.

After 3 weeks of ultrasound treatment there are marked differences visible between histology images of tissue from the control animals (FIG. 20A) and the ultrasound-treated animals (FIG. 20B). In the ultrasound-treated grafts there is cellular infiltration of fibrous tissue into the tendon in between the tendon fascicles. There is neo-angiogenesis/vascularity shown in the 20× magnification image, indicated by the arrows. The graft is highly cellular and the cells are plump active (matrix producing) cells. By contrast, the control samples (FIG. 20A) show no evidence of vascularity, the cells within the graft are necrotic, and the tendon is starting to degenerate.

Figure 21A:
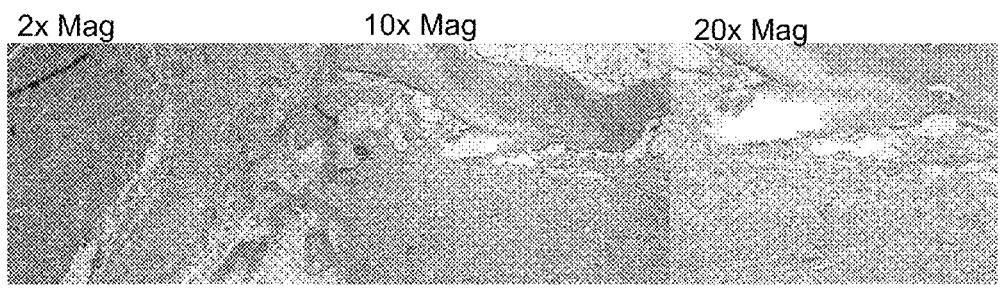
FIG. 21A is a photomicrograph of ovine tendon graft after 6 weeks without treatment according to the invention.
Figure 21B:
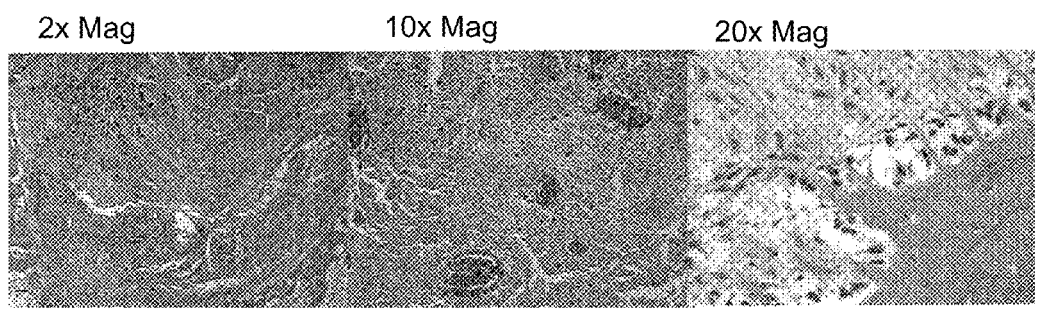
FIG. 21B is a photomicrograph of ovine tendon graft after 6 weeks with ultrasonic treatment according to the invention.
Figure 21C:
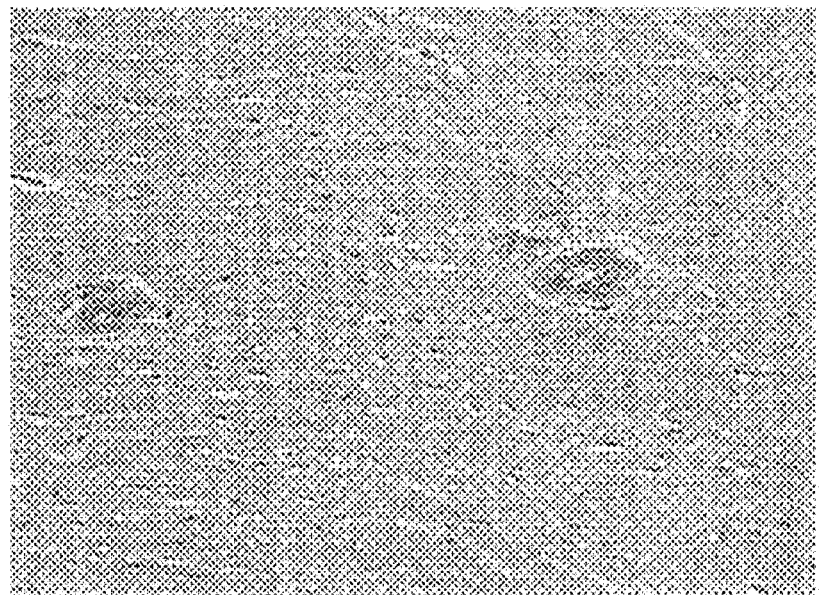
FIG. 21C is a photomicrograph of an intra-articular section of the ovine tendon graft shown after 6 weeks with ultrasonic treatment according to the invention.
Figure 21D:
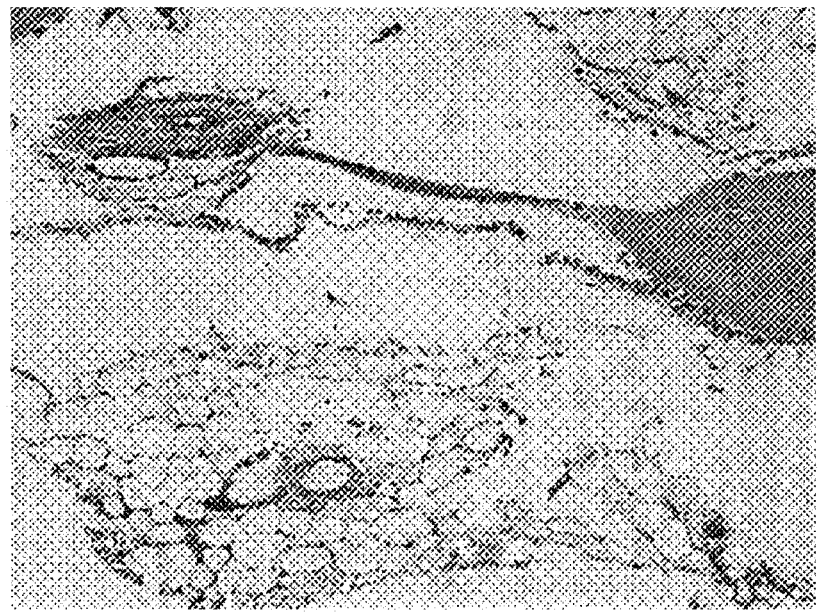
FIG. 21D is a photomicrograph of bone marrow near an ovine tendon graft after 6 weeks with ultrasonic treatment according to the invention.

After 6 weeks of ultrasound there is extensive neoangiogenesis in the graft, as shown in FIG. 21B. The black dots in the 2× magnification picture are all new blood vessels. The red blood cells within these vessels can be seen in the 10× magnification image. At 20× magnification there are viable cells throughout the graft and there is new bone deposition and Sharpey's fibres at the interface of the graft and the bone tunnel. The Sharpey's fibres are spicules of bone that anchor the graft into the bone tunnel. By contrast, the control histology images shown in FIG. 21A show very little evidence of vascularity. The cells within the tendon body are very sparse and there is little evidence of Sharpey's fibres at the bone tendon interface. After six weeks of ultrasound treatment the angiogenic response is very pronounced that the intra-articular section of the graft and the bone marrow contained new blood vessels, as shown in FIGS. 21C and 21D, respectively.

Figure 22A:
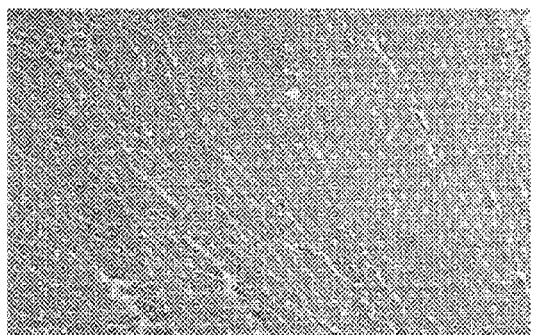
FIG. 22A is a photomicrograph of an intra-articular section of ovine tendon graft after 12 weeks without treatment.
Figure 22B:
FIG. 22B is a photomicrograph of an intra-articular section of ovine tendon graft after 12 weeks with ultrasonic treatment according to the invention.
Figure 22C:
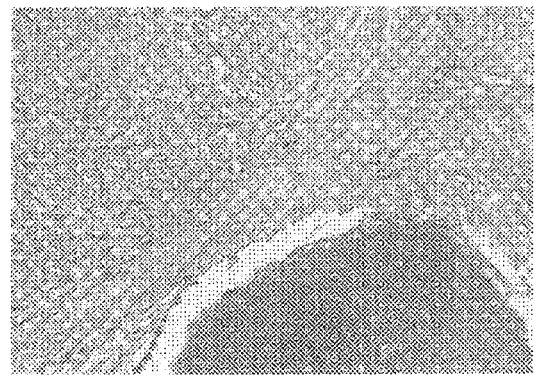
FIG. 22C is a photomicrograph of ovine tendon graft after 12 weeks without treatment.
Figure 22D:
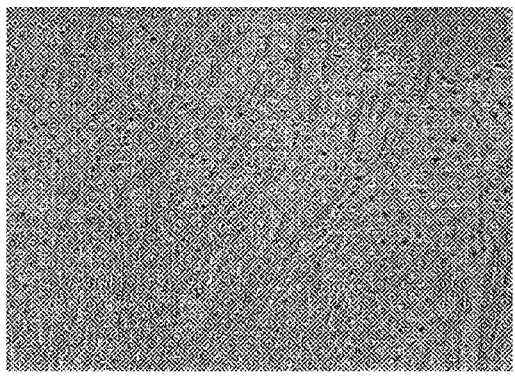
FIG. 22D is a photomicrograph of ovine tendon graft after 12 weeks with ultrasonic treatment according to the invention.

At 12 weeks, the intra-articular section of the graft in the control group, shown in FIG. 22A is essentially dead, with very few cells and blood vessels. By contrast, the ultrasound treated graft, shown in FIG. 22B, is highly cellular and contains functional blood vessels containing red blood cells. Photomicrographs of the treated graft show that there is a mature tissue at the bone tendon interface with healthy active cells after ultrasound treatment, shown in FIG. 22D. There are many Sharpey's fibres infiltrating the graft, which will provide increased strength. By contrast, photomicrographs of the control graft, FIG. 22C show few cells, which are to producing a loose fibrous tissue, and few Sharpey's fibres at the bone tendon interface.

EXAMPLE 2

Hartley strain guinea pigs that spontaneously develop osteoarthritis (OA) were used for this study. This strain develops an arthropathology that mimics human OA between the age of 6 and 12 months of age. The OA is confined to the medial tibia plateau in the early stages of the disease.

Eight animals were utilized for this study. The animals were 2 months of age when the study was initiated. The left legs of the animals were treated with pulsed low intensity ultrasound (1.5 MHz, pulsed at 1 KHz, 200 µs burst width) for a period of 4 months. The ultrasound was applied for 20 minutes per day, for 5 days per week. The ultrasound transducer was coupled to the skin with gel on the media side of the left knee after first shaving the knee joint. The transducers were held in place during treatment with strapping. The animals were terminated at 6 months of age after 4 months of treatment.

Figure 23A:
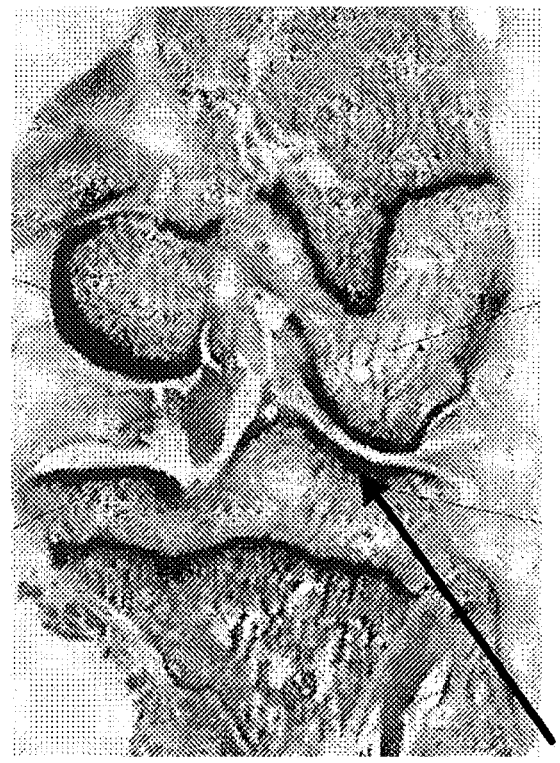
FIG. 23A is a photomicrograph of tissue from an ultrasound treated knee joint in a guinea pig having osteoarthritis.
Figure 23B:
FIG. 23B is a photomicrograph of tissue from a control knee joint in a guinea pig having osteoarthritis.

The ultrasound treated (FIG. 23A) and control (FIG. 23B) knee joints were dissected and decalcified in 10% formic acid-formalin solution. The knee joints were then embedded in paraffin. Five-micron thick sections were cut on a microtome and stained with toluidine blue for microscopic analysis. After 4 months of ultrasound treatment there was a marked difference in the degree/severity of OA between the treated and control knees. The cartilage on the media tibia plateau of ultrasound treated knee remained intact, as shown in FIG. 23A, whereas the cartilage on the control knee showed signs of degeneration, as shown in FIG. 23B. This observation (cartilage thinning, defects and surface irregularities) was consistently observed in animals that developed OA by 6 months of age.

It will be understood that various modifications can be made to the various embodiments of the present invention herein disclosed without departing from its spirit and scope. For example, various modifications may be made in the structural configuration of the placement modules and the configuration of the components used to excite the ultrasonic transducer. Therefore the above description should not be construed as limiting the invention by merely as presenting preferred embodiments of the invention. Those skilled in the art will envision other modifications within the scope and spirit of the present invention as defined by the claims presented below.

What is claimed is:

1. A method for stimulating growth or healing, or treating pathologies, of a spinal disc in mammals in need thereof, comprising:
subjecting the affected spinal disc to noninvasive, low intensity pulsed ultrasound with a substantially single frequency between about 1 MHz and about 2 MHz, a pulse width of between about 10 and about 2,000 microseconds, a repetition frequency of about 0.1 to about 10 KHz, and for a duration sufficient to stimulate growth, healing, or repair of the spinal disc.

2. The method of claim 1 wherein the low intensity ultrasound has a frequency of around 1.5 MHz.

3. The method of claim 1 wherein the pulse width is about 200 microseconds.

4. The method of claim 1, wherein the repetition frequency is about 1 KHz.

5. The method of claim 1, wherein the intensity of the ultrasound is less than 100 milliwatts/cm$^2$.

6. The method of claim 1, wherein the spinal disc is affected by a degenerative disease.

7. The method of claim 1, wherein subjecting the affected spinal disc to the noninvasive, low intensity pulsed ultrasound for a duration sufficient to stimulate growth, healing, or repair of the spinal disc comprises subjecting the affected spinal disc to the noninvasive, low intensity pulsed ultrasound for a duration sufficient to stimulate growth, healing, or repair of connective tissue of the spinal disc.

* * * * *